(12) United States Patent
Chen et al.

(10) Patent No.: US 9,371,535 B2
(45) Date of Patent: Jun. 21, 2016

(54) BACTERIAL XYLOSE ISOMERASES ACTIVE IN YEAST CELLS

(71) Applicant: E I DU PONT DE NEMOURS AND COMPANY, Wilmington, DE (US)

(72) Inventors: Zhongqiang Chen, Wilmington, DE (US); Kristen J Kelly, Wilmington, DE (US); Rick W Ye, Hockessin, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

(21) Appl. No.: 14/881,563

(22) Filed: Oct. 13, 2015

(65) Prior Publication Data

US 2016/0130590 A1     May 12, 2016

Related U.S. Application Data

(62) Division of application No. 13/792,321, filed on Mar. 11, 2013, now Pat. No. 9,187,743.

(51) Int. Cl.
*C12N 1/14* (2006.01)
*C12N 15/81* (2006.01)
*C12N 9/92* (2006.01)

(52) U.S. Cl.
CPC *C12N 15/81* (2013.01); *C12N 9/92* (2013.01); *C12Y 503/01005* (2013.01)

(58) Field of Classification Search
CPC ........................................................ C12N 15/81
USPC ..................................................... 435/254.2
See application file for complete search history.

(56) References Cited

U.S. PATENT DOCUMENTS

| | | | |
|---|---|---|---|
| 5,686,276 A | 11/1997 | Laffend et al. | |
| 6,013,494 A | 1/2000 | Nakamura et al. | |
| 6,514,733 B1 | 2/2003 | Emptage et al. | |
| 7,005,291 B1 | 2/2006 | Nair et al. | |
| 7,622,284 B2 | 11/2009 | Op Den Camp et al. | |
| 7,629,151 B2 | 12/2009 | Gold et al. | |
| 7,851,188 B2 | 12/2010 | Donaldson et al. | |
| 7,943,366 B2 | 5/2011 | Rajgarhia et al. | |
| 8,058,040 B2 | 11/2011 | Op Den Camp et al. | |
| 8,093,037 B2 | 1/2012 | Picataggio et al. | |
| 8,114,974 B2 | 2/2012 | Picataggio et al. | |
| 8,129,171 B2 | 3/2012 | Boles et al. | |
| 8,206,970 B2 | 6/2012 | Eliot et al. | |
| 2006/0216804 A1 | 9/2006 | Karhumaa | |
| 2007/0155000 A1 | 7/2007 | Nilsson et al. | |
| 2007/0292927 A1 | 12/2007 | Donaldson et al. | |
| 2008/0182308 A1 | 7/2008 | Donaldson et al. | |
| 2009/0061502 A1 | 3/2009 | Nilsson et al. | |
| 2009/0155870 A1 | 6/2009 | Donaldson et al. | |
| 2010/0028975 A1 | 2/2010 | Gorwa-Grauslund | |
| 2010/0112658 A1 | 5/2010 | Hughes et al. | |
| 2011/0318801 A1 | 12/2011 | Kahsay et al. | |
| 2012/0184020 A1 | 7/2012 | Picataggio et al. | |

FOREIGN PATENT DOCUMENTS

| | | |
|---|---|---|
| EP | 2626423 A1 | 8/2013 |
| WO | 2006115455 A1 | 11/2006 |
| WO | 2011078262 A1 | 6/2011 |
| WO | 2011079388 A1 | 7/2011 |
| WO | 2011149353 A1 | 12/2011 |
| WO | 2011153516 A2 | 12/2011 |
| WO | 2012009272 A2 | 1/2012 |
| WO | 2013003219 A1 | 1/2013 |
| WO | 2626423 A1 | 8/2013 |

OTHER PUBLICATIONS

Database Accession No. J4UBX7, UniProt, Oct. 31, 2012.
Database Accession No. K0XJX8, UniProt, Nov. 28, 2012.
Database Accession No. F3B0S7, UniProt, Jun. 28, 2011.
Database Accession No. H1LTI3, UniProt, Mar. 21, 2012.
Database Accession No. E6LP05, UniProt, Mar. 8, 2011.
International Search Report dated Jul. 9, 2014, International Application No. PCT/US2014/022358.
GenBank Accession No. ZP_04453767.
U.S. Appl. No. 13/792,308, filed Mar. 11, 2013.
U.S. Appl. No. 13/792,668, filed Mar. 11, 2013.
Matsushika, Akinori et al., Ethanol production from xylose in engineered *Saccharomyces cerevisiae* strains: current state and perspectives, Applied Microbiology and Biotechnology, 2009, pp. 37-53, vol. 84.
Kuyper, Marko et al., Metabolic engineering of a xylose-isomerase-expressing *Saccharomyces cerevisiae* strain for rapid anaerobic xylose fermentation, FEMS Yeast Research, 2005, pp. 399-409, vol. 5.
U.S. Appl. No, 13/792,308, filed Mar. 11, 2013.
Matsushika, Akinori et al., Ethanol production from xylose in engineered *Saccharomyces cerevisiae* strains: current state and perspectives, Applied Microbiology and Biotechnology, 2009, pp, 37-53, vol. 84.
Kuyper, Marko et al., Metabolic engineering of a xyiose-isomerase-expressing *Saccharomyces cerevisiae* strain for rapid anaerobic xyiose fermentation, FEMS Yeast Research, 2005, pp. 399-409, vol. 5.
Database Accession No. K0XJK8, Uniprot, Nov. 28, 2012.
Database Accession No. F3B0S7, Uniprot, Jun. 23, 2011.
Database Accesssion No. H1LT13, Uniprot, March 21, 2012.
International Search Report Dated Jul. 9, 2014 International Application No. PCT/US2014/022358.

*Primary Examiner* — Tekchand Saidha

(57) ABSTRACT

Specific polypeptides were identified as bacterial xylose isomerases that are able to provide xylose isomerase activity in yeast cells. The xylose isomerase activity can complete a xylose utilization pathway so that yeast can use xylose in fermentation, such as xylose in biomass hydrolysate.

9 Claims, No Drawings

BACTERIAL XYLOSE ISOMERASES ACTIVE IN YEAST CELLS

CROSS-REFERENCE TO RELATED APPLICATIONS

This application is a divisional of and claims the benefit of priority to U.S. patent application Ser. No. 13/792,321, filed on Mar. 11, 2013 now U.S. Pat. No. 9,187,743, the entirety of which is herein incorporated by reference.

FIELD OF THE INVENTION

The invention relates to the field of genetic engineering of yeast. More specifically, a group of xylose isomerases are identified that are active in yeast cells engineered for their expression.

BACKGROUND OF THE INVENTION

Currently yeasts are the organism or choice for the fermentative production of ethanol. Most common is the use of *Saccharomyces cerevisiae*, in processes using hexoses obtained from grains or mash as the carbohydrate source. Use of hydrolysate prepared from cellulosic biomass as a carbohydrate source for fermentation is desirable, as this is a readily renewable resource that does not compete with the food supply.

After glucose, the second most abundant sugar in cellulosic biomass is xylose, a pentose. *Saccharomyces cerevisiae* is not naturally capable of metabolizing xylose, but can be engineered to metabolize xylose with expression of xylose isomerase activity to convert xylose to xylulose, and additional pathway engineering.

Success in expressing heterologous bacterial xylose isomerase enzymes that are active in yeast has been limited. Some specific xylose bacterial isomerase sequences have been reported to provide xylose isomerase activity for a xylose utilization pathway in yeast. For example as U.S. Pat. No. 7,622,284 discloses a yeast cell expressing a xylose isomerase from *Piromyces* sp. US 2012/0184020 discloses eukaryotic cells expressing a xylose isomerase isolated from *Ruminococcus flavefaciens*. Similarly WO2011078262 disclose several xylose isomerases from each of *Reticulitermes speratus* and *Mastotermes darwiniensis* and proteins with high sequence identities to these, and their expression in eukaryotic cells. WO212009272 discloses constructs and fungal cells containing a xylose isomerase from *Abiotrophia defectiva* and others with sequence identity to it.

There remains a need for additional engineered yeast cells that express xylose isomerase activity for successful utilization of xylose, thereby allowing effective use of sugars obtained from cellulosic biomass during fermentation.

SUMMARY OF THE INVENTION

The invention provides recombinant yeast cells that are engineered to express a polypeptide that provides xylose isomerase activity.

Accordingly, the invention provides a recombinant yeast cell comprising a heterologous nucleic acid molecule encoding a polypeptide having xylose isomerase activity and amino acid sequence with at least about 85% sequence identity to an amino acid sequence selected from the group consisting of SEQ ID NOs:1, 3, 5, and 7.

In another aspect the invention provides a method for producing a yeast cell that has xylose isomerase activity comprising:
 a) providing a yeast cell;
 b) introducing a heterologous nucleic acid molecule encoding a polypeptide having xylose isomerase activity and amino acid sequence with at least about 85% sequence identity to an amino acid sequence selected from the group consisting of SEQ ID NOs:1, 3, 5, and 7;
wherein a yeast cell having xylose isomerase activity is produced.

SEQUENCE DESCRIPTIONS

The invention can be more fully understood from the following detailed description and the accompanying sequence descriptions which form a part of this application.

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (2009) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

TABLE 1

SEQ ID NOs for xylose isomerase polypeptides, and coding regions that are codon optimized for expression in *S. cerevisiae*

| Strain | SEQ ID NO: amino acid | SEQ ID NO: nucleotide codon opt. |
|---|---|---|
| *Lachnospiraceae bacterium* ICM7 | 1 | 2 |
| *Lachnospiraceae bacterium* oral taxon 107 str. F0167 | 3 | 4 |
| *Lachnospiraceae bacterium* oral taxon 082 str. F0431 | 5 | 6 |
| *Eubacterium saburreum* DSM 3986 | 7 | 8 |
| *Ruminococcus champanellensis* 18P13 | 9 | 10 |
| *Ruminococcus flavefaciens* FD-1 | 11 | *nd |
| *Abiotrophis defectiva* | 12 | *nd |
| *Leptotrichia goodfellowii* F0264 | 13 | 14 |
| *Sebaldella termitidis* ATCC 33386 | 15 | 16 |

*nd = not designed

SEQ ID NO:17 is the nucleotide sequence of the pHR81 vector containing the ILVp-xylA(Hm1)-ILV5t chimeric gene.

SEQ ID NO:18 is the nucleotide sequence of P5 Integration Vector.

SEQ ID NO:19 is the nucleotide sequence of a URA3 deletion scar.

SEQ ID NO:20 is the nucleotide sequence of the upstream ura3Δ, post deletion region.

SEQ ID NO:21 is the nucleotide sequence of the downstream ura3Δ post deletion region.

SEQ ID NO:22 is the nucleotide sequence of the upstream his3Δ, post deletion region.

SEQ ID NO:23 is the nucleotide sequence of the downstream his3Δ post deletion region.

SEQ ID NO:24 is the nucleotide sequence of pJT254.

DETAILED DESCRIPTION

The following definitions may be used for the interpretation of the claims and specification:

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the specification and the claims.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value.

The term "xylose isomerase" refers to an enzyme that catalyzes the interconversion of D-xylose and D-xylulose. Xylose isomerases (XI) belong to the group of enzymes classified as EC 5.3.1.5.

The terms "xylose utilization pathway" refers to a metabolic pathway comprising genes encoding enzymes sufficient to convert xylose to a target chemical. In the situation where the target chemical is ethanol such a pathway typically comprises genes encoding the following enzymes: xylulokinase (XKS1), transaldolase (TAL1), transketolase 1 (TKL1), D-ribulose-5-phosphate 3-epimerase (RPE1), and ribose 5-phosphate ketol-isomerase (RKI1). Elements of this pathway may be native or heterologous to the host cell.

The term "gene" refers to a nucleic acid fragment that expresses a specific protein or functional RNA molecule, which may optionally include regulatory sequences preceding (5' non-coding sequences) and following (3' non-coding sequences) the coding sequence. "Native gene" or "wild type gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes.

The term "promoter" or "Initiation control regions" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters".

The term "expression", as used herein, refers to the transcription and stable accumulation of coding (mRNA) or functional RNA derived from a gene. Expression may also refer to translation of mRNA into a polypeptide. "Overexpression" refers to the production of a gene product in transgenic organisms that exceeds levels of production in normal or non-transformed organisms.

The term "transformation" as used herein, refers to the transfer of a nucleic acid fragment into a host organism, resulting in genetically stable inheritance. The transferred nucleic acid may be in the form of a plasmid maintained in the host cell, or some transferred nucleic acid may be integrated into the genome of the host cell. Host organisms containing the transformed nucleic acid fragments are referred to as "transgenic" or "recombinant" or "transformed" organisms.

The terms "plasmid" and "vector" as used herein, refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "selectable marker" means an identifying factor, usually an antibiotic or chemical resistance gene, that is able to be selected for based upon the marker gene's effect, i.e., resistance to an antibiotic, wherein the effect is used to track the inheritance of a nucleic acid of interest and/or to identify a cell or organism that has inherited the nucleic acid of interest.

As used herein the term "codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA.

The term "carbon substrate" or "fermentable carbon substrate" refers to a carbon source capable of being metabolized by microorganisms. A type of carbon substrate is "fermentable sugars" which refers to oligosaccharides and monosaccharides that can be used as a carbon source by a microorganism in a fermentation process.

The term "lignocellulosic" refers to a composition comprising both lignin and cellulose. Lignocellulosic material may also comprise hemicellulose.

The term "cellulosic" refers to a composition comprising cellulose and additional components, which may include hemicellulose and lignin.

The term "saccharification" refers to the production of fermentable sugars from polysaccharides.

The term "pretreated biomass" means biomass that has been subjected to thermal, physical and/or chemical pretreatment to increase the availability of polysaccharides in the biomass to saccharification enzymes.

"Biomass" refers to any cellulosic or lignocellulosic material and includes materials comprising cellulose, and optionally further comprising hemicellulose, lignin, starch, oligosaccharides and/or monosaccharides. Biomass may also comprise additional components, such as protein and/or lipid. Biomass may be derived from a single source, or biomass can comprise a mixture derived from more than one source; for example, biomass could comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn cobs, crop residues such as corn husks, corn stover, corn grain fiber, grasses, beet pulp, wheat straw, wheat chaff, oat straw, barley straw, barley hulls, hay, rice straw, rice hulls, switchgrass, miscanthus, cord grass, reed canary grass, waste paper, sugar cane bagasse, sorghum bagasse, sorghum stover, soybean stover, components obtained from milling of grains, trees, branches, roots, leaves, wood chips, sawdust, palm waste, shrubs and bushes, vegetables, fruits, flowers, and animal manure.

"Biomass hydrolysate" refers to the product resulting from saccharification of biomass. The biomass may also be pretreated or pre-processed prior to saccharification.

The term "heterologous" means not naturally found in the location of interest. For example, a heterologous gene refers to a gene that is not naturally found in the host organism, but that is introduced into the host organism by gene transfer. For example, a heterologous nucleic acid molecule that is present in a chimeric gene is a nucleic acid molecule that is not naturally found associated with the other segments of the chimeric gene, such as the nucleic acid molecules having the coding region and promoter segments not naturally being associated with each other.

As used herein, an "isolated nucleic acid molecule" is a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

The term "target compound" or "target chemical" refers to a compound made by a microorganism via an endogenous or recombinant biosynthetic pathway which is able to metabolize a fermentable carbon source to produce the target compound.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991).

Preferred methods to determine identity are designed to give the best match between the sequences tested. Methods to determine identity and similarity are codified in publicly available computer programs. Sequence alignments and percent identity calculations may be performed using the MegAlign program of the LASERGENE bioinformatics computing suite (DNASTAR Inc., Madison, Wis.).

Multiple alignment of the sequences is performed using the "Clustal method of alignment" which encompasses several varieties of the algorithm including the "Clustal V method of alignment" corresponding to the alignment method labeled Clustal V (described by Higgins and Sharp, CABIOS. 5:151-153 (1989); Higgins, D. G. et al., *Comput. Appl. Biosci.*, 8:189-191 (1992)) and found in the MegAlign v8.0 program of the LASERGENE bioinformatics computing suite (DNASTAR Inc.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program.

Additionally the "Clustal W method of alignment" is available and corresponds to the alignment method labeled Clustal W (described by Higgins and Sharp, *CABIOS*. 5:151-153 (1989); Higgins, D. G. et al., *Comput. Appl. Biosci*. 8:189-191(1992); Thompson, J. D. et al, Nucleic Acid Research, 22 (22): 4673-4680, 1994) and found in the MegAlign v8.0 program of the LASERGENE bioinformatics computing suite (DNASTAR Inc.). Default parameters for multiple alignment (stated as protein/nucleic acid (GAP PENALTY=10/15, GAP LENGTH PENALTY=0.2/6.66, Delay Divergen Seqs(%)=30/30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program. Sequence identities referred to herein shall always be considered to have been determined according to the parameters set forth above unless otherwise noted.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., J. Mol. Biol., 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, Comput. Methods Genome Res., [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

Standard recombinant DNA and molecular cloning techniques used herein are well known in the art and are described by Sambrook, J. and Russell, D., *Molecular Cloning: A Laboratory Manual*, Third Edition, Cold Spring Harbor Laboratory Press, Cold Spring Harbor, N.Y. (2001); and by Silhavy, T. J., Bennan, M. L. and Enquist, L. W., *Experiments with Gene Fusions*, Cold Spring Harbor Laboratory Press, Cold Spring Harbor, N.Y. (1984); and by Ausubel, F. M. et. al., *Short Protocols in Molecular Biology*, 5$^{th}$ Ed. Current Protocols, John Wiley and Sons, Inc., N.Y., 2002. Additional methods used here are in *Methods in Enzymology*, Volume 194, *Guide to Yeast Genetics and Molecular and Cell Biology* (Part A, 2004, Christine Guthrie and Gerald R. Fink (Eds.), Elsevier Academic Press, San Diego, Calif.).

The present invention relates to engineered yeast strains that have xylose isomerase enzyme activity. A challenge for engineering yeast to utilize xylose, which is the second most predominant sugar obtained from cellulosic biomass, is to produce sufficient xylose isomerase activity in the yeast cell. Xylose isomerase catalyzes the conversion of xylose to xylulose, which is the first step in a xylose utilization pathway. Applicants have found that expression of specific xylose isomerase polypeptides provides xylose isomerase activity in the yeast cell, while expression of other xylose isomerase polypeptides does not provide activity. A yeast cell expressing xylose isomerase activity provides a host cell for expression of a complete xylose utilization pathway, thereby engineering a yeast cell that can produce a target compound, such as ethanol, butanol, or 1,3-propanediol, using xylose derived from lignocellulosic biomass as a carbon source.
Yeast Host Cells Yeast cells of the invention are those that comprise a functional bacterial xylose isomerase and a capable of the production of a target compound. Preferred target compounds are those of commercial value including but not limited to ethanol, butanol, or 1,3-propanediol.

Any yeast cells that either produce a target chemical, or can be engineered to produce a target chemical, may be used as host cells herein. Examples of such yeasts include, but are not limited to, yeasts of the genera *Kluyveromyces, Candida, Pichia, Hansenula, Schizosaccharomyces, Kloeckera, Schwammiomyces, Yarrowia*, and *Saccharomyces*.

Yeast cells of the invention comprising an active bacterial xylose isomerase may be engineered according to methods well known in the art. For example yeast cell that have the native ability to produce ethanol from C6 sugars may be transferred with genes comprising C5 metabolic pathways including the bacterial xylose isomerase of the invention. Such cells may be capable of either aerobic or anaerobic fermentive ethanol production.

In other embodiments yeast cells may be engineered to express a pathway for synthesis of butanol or 1,3-propanediol. Engineering of pathways for butanol synthesis (including isobutanol, 1-butanol, and 2-butanol) have been disclosed, for example in U.S. Pat. No. 8,206,970, US 20070292927, US 20090155870, U.S. Pat. No. 7,851,188, and US 20080182308, which are incorporated herein by reference. Engineering of pathways for 1,3-propanediol have been disclosed in U.S. Pat. No. 6,514,733, U.S. Pat. No. 5,686,276, U.S. Pat. No. 7,005,291, U.S. Pat. No. 6,013,494, and U.S. Pat. No. 7,629,151, which are incorporated herein by reference.

For utilization of xylose as a carbon source, a yeast cell is engineered for expression of a complete xylose utilization pathway. Engineering of yeast such as *S. cerevisiae* for production of ethanol from xylose is described in Matsushika et al. (Appl. Microbiol. Biotechnol. (2009) 84:37-53) and in Kuyper et al. (FEMS Yeast Res. (2005) 5:399-409). In one embodiment, in addition to engineering a yeast cell as disclosed herein to have xylose isomerase activity, the activities of other pathway enzymes are increased in the cell to provide the ability to grow on xylose as a sole carbon source. Typically the activity levels of five pentose pathway enzymes are increased: xylulokinase (XKS1), transaldolase (TAL1), transketolase 1 (TKL1), D-ribulose-5-phosphate 3-epimerase (RPE1), and ribose 5-phosphate ketol-isomerase (RKI1). Any method known to one skilled in the art for increasing expression of a gene may be used. For example, as described herein in Example 1, these activities may be increased by expressing the host coding region for each protein using a highly active promoter. Chimeric genes for expression are constructed and are integrated into the yeast genome. Alternatively, heterologous coding regions for these enzymes may be expressed in the yeast cell to obtain increased enzyme activities. For additional methods for engineering yeast capable of metabolizing xylose see for example U.S. Pat. No. 7,622,284B2, U.S. Pat. No. 8,058,040B2, U.S. Pat. No. 7,943,366 B2, WO2011153516A2, WO2011149353A1, WO2011079388A1, US20100112658A1, US20100028975A1, US20090061502A1, US20070155000A1, WO2006115455A1, US20060216804A1 and U.S. Pat. No. 8,129,171B2

In one embodiment the present yeast cell has xylose isomerase activity as described below, and additional genetic engineering to provide a complete xylose utilization pathway as described above. These cells are able to grow in medium containing xylose as the sole carbon source. More typically, these cells are grown in medium containing xylose as well as other sugars such as glucose and arabinose. This allows effective use of the sugars found in a hydrolysate medium that is prepared from cellulosic biomass by pretreatment and saccharification.

Xylose Isomerase

Expression of xylose isomerases in yeast cells has been problematic; in particular, many bacterial xylose isomerases have been found to have little to no activity when expressed in yeast cells. In the present recombinant yeast cell, xylose isomerase activity is provided by expression of a heterologous nucleic acid molecule encoding a polypeptide having an amino acid sequence with at least about 85% sequence identity to an amino acid sequence of SEQ ID NO:1, 3, 5, or 7. These sequences were identified by BLAST searching of the GenBank database (National Center for Biotechnology Information (NCBI); Benson et al. Nucleic Acids Research, 2011 January; 39 (Database issue):D32-7) using xylose isomerase sequences from *Ruminococcus flavefaciens* FD-1 (SEQ ID NO:11) and from *Ruminococcus champanellensis* 18P13 (SEQ ID NO:9). SEQ ID NO:11 is identical to the *Ruminococcus flavefaciens* xylose isomerase of SEQ ID NO:31 in US 2012/0184020.

SEQ ID NOs:1, 3, 5, and 7 are the amino acid sequences of bacterial xylose isomerases from *Lachnospiraceae bacterium* ICM7 (called herein Hm1), *Lachnospiraceae bacterium* oral taxon 107 str. F0167 (called herein Hm2), *Lachnospiraceae bacterium* oral taxon 082 str. F0431 (called herein Hm3), and *Eubacterium saburreum* DSM 3986 (called herein Hm4), respectively. The identities of these four sequences to the *Ruminococcus flavefaciens* FD-1 (SEQ ID NO:11) and *Ruminococcus champanellensis* 18P13 (SEQ ID NO:9) sequences are between 60.9% and 62.6% as given in Table 2. The identities of these four sequences to a hypothetical protein from *Abiotrophis defectiva* ATCC 49176 (SEQ ID NO:12; Accession #ZP 04453767), which is identical to SEQ ID NO:2 of WO 2102/009272 and is identified therein as *Abiotrophia defectiva* xylose isomerase, are between 71.7% and 73.2% as given in Table 2.

Expression of a nucleic acid molecules encoding Hm1, Hm2, Hm3, and Hm4 in *S. cerevisiae* was found herein (Example 3) to allow growth in medium containing xylose as the sole sugar, of a *S. cerevisiae* strain containing a xylose utilization pathway but lacking xylose isomerase activity. Xylose was utilized and ethanol was produced by the yeast cells. Thus expression of each of HM1, Hm2, Hm3, and Hm4 provided xylose isomerase activity to complete the xylose utilization pathway in the yeast cells. Among Hm1, Hm2, Hm3, and Hm4 the sequence identities are in the range of 92.2% to 95.7% as given in Table 2.

Any polypeptide having xylose isomerase activity and having at least about 85% identity to any of SEQ ID NO:1, 3, 5, and 7 may be expressed in the present yeast cell. In various embodiments the polypeptide may have amino acid sequence identity of about 85%, 86%, 87%, 88%, 89%, 90%, 91%, 92%, 93%, 94%, 95%, 96%, 97%, 98%, 99% or up to 100% to any of SEQ ID NO:1, 3, 5, and 7.

When transformed with the xylose isomerase of the invention a *S. cerevisiae* demonstrated increase growth, xylose utilization and ethanol yield when grown in xylose containing medium. Xylose isomerase proteins, having as much as 95% identity to SEQ ID NO:1, 3, 5, and 7 did not have the same effect, suggesting that the ability of the enzyme to be active in a yeast host may not be sequence dependent. Specifically, sequences from *Leptotrichia goodfellowii* F0264 (called herein Oral-2; SEQ ID NO:13) and *Sebaldella termitidis* ATCC 33386 (called herein Term-1; SEQ ID NO:15) have similar sequence identities to the *Ruminococcus flavefaciens* FD-1 (SEQ ID NO:11) and *Ruminococcus champanellensis* 18P13 (SEQ ID NO:9) xylose isomerases (see Table 2) as Hm1, Hm2, Hm3, and Hm4, but did not provide xylose isomerase activity in yeast cells as tested in Example 3 herein.

TABLE 2

Comparison of xylose isomerase amino acid sequence identities

| | Hm1 | Hm2 | Hm3 | Hm4 | Oral2 | Term 1 | R. f. XI | R. c. XI |
|---|---|---|---|---|---|---|---|---|
| Hm1 | | | | | | | | |
| Hm2 | 95.5 | | | | | | | |
| Hm3 | 93.6 | 92.3 | | | | | | |
| Hm4 | 92.9 | 93.2 | 95.7 | | | | | |
| Leptotrichia goodfellowii F0264 (Oral2) | 57.4 | 57.2 | 56.1 | 57.0 | | | | |
| Sebaldella termitidis ATCC 33386 (Term1) | 55.8 | 55.1 | 54.9 | 55.8 | 85.2 | | | |
| XI from R. flavefaciens | 62.2 | 61.5 | 60.9 | 60.9 | 61.7 | 59.9 | | |
| XI from R. champanellensis | 62.6 | 61.9 | 61.8 | 62.2 | 60.7 | 61.2 | 77.4 | |
| XI from A. defectiva | 73.2 | 72.5 | 71.7 | 72.1 | 57.4 | 54.9 | 61.9 | 61.0 |

The present amino acid sequences that provide xylose isomerase activity in yeast cells are not native to yeast cells, thus their encoding nucleic acid sequences are heterologous to yeast cells. For expression, nucleic acid molecules encoding the present polypeptides may be designed using codon optimization for the desired yeast cell, as is well known to one skilled in the art. For example, for expression of HM1, Hm3, Hm5, or Hm7 in *Saccharomyces cerevisiae*, nucleic acid molecules named xylA(Hm1) (SEQ ID NO:2), xylA(Hm2) (SEQ ID NO:4), xylA(Hm3) (SEQ ID NO:6), and xylA(Hm4) (SEQ ID NO:8) were designed using codon-optimization for expression *S. cerevisiae*.

Methods for gene expression in yeasts are known in the art (see for example *Methods in Enzymology*, Volume 194, *Guide to Yeast Genetics and Molecular and Cell Biology* (Part A, 2004, Christine Guthrie and Gerald R. Fink (Eds.), Elsevier Academic Press, San Diego, Calif.). Expression of genes in yeast typically requires a promoter, operably linked to the coding region of interest, and a transcriptional terminator. A number of yeast promoters can be used in constructing expression cassettes for genes encoding the desired proteins, including, but not limited to constitutive promoters FBA1, GPD1, ADH1, GPM, TPI1, TDH3, PGK1, ILV5p, and the inducible promoters GAL1, GAL10, and CUP1. Suitable transcription terminators include, but are not limited to FBAt, GPDt, GPMt, ERG10t, GAL1t, CYC1t, ADH1t, TAL1 t, TKL1t, ILV5t, and ADHt.

Suitable promoters, transcriptional terminators, and coding regions may be cloned into *E. coli*-yeast shuttle vectors, and transformed into yeast cells. These vectors allow strain propagation in both *E. coli* and yeast strains.

Typically the vector contains a selectable marker and sequences allowing autonomous replication or chromosomal integration in the desired host. Typically used plasmids in yeast are shuttle vectors pRS423, pRS424, pRS425, and pRS426 (American Type Culture Collection, Rockville, Md.), which contain an *E. coli* replication origin (e.g., pMB1), a yeast 2µ origin of replication, and a marker for nutritional selection. The selection markers for these four vectors are His3 (vector pRS423), Trp1 (vector pRS424), Leu2 (vector pRS425) and Ura3 (vector pRS426). Additional vectors that may be used include pHR81 (ATCC #87541) and pRS313 (ATCC #77142). Construction of expression vectors with chimeric genes encoding the desired proteins may be performed by either standard molecular cloning techniques in *E. coli* or by the gap repair recombination method in yeast.

The gap repair cloning approach takes advantage of the highly efficient homologous recombination in yeast. Typically, a yeast vector DNA is digested (e.g., in its multiple cloning site) to create a "gap" in its sequence. The "gapped" vector and insert DNAs having sequentially overlapping ends (overlapping with each other and with the gapped vector ends, in the desired order of inserts) are then co-transformed into yeast cells which are plated on the medium containing the appropriate compound mixtures that allow complementation of the nutritional selection markers on the plasmids. The presence of correct insert combinations can be confirmed by PCR mapping using plasmid DNA prepared from the selected cells. The plasmid DNA isolated from yeast can then be transformed into an *E. coli* strain, e.g. TOP10, followed by mini preps and restriction mapping to further verify the plasmid construct. Finally the construct can be verified by sequence analysis.

Like the gap repair technique, integration into the yeast genome also takes advantage of the homologous recombination system in yeast. Typically, a cassette containing a coding region plus control elements (promoter and terminator) and auxotrophic marker is PCR-amplified with a high-fidelity DNA polymerase using primers that hybridize to the cassette and contain 40-70 base pairs of sequence homology to the regions 5' and 3' of the genomic area where insertion is desired. The PCR product is then transformed into yeast cells which are plated on medium containing the appropriate compound mixtures that allow selection for the integrated auxotrophic marker. Transformants can be verified either by colony PCR or by direct sequencing of chromosomal DNA.

The present invention provides a method for producing a yeast cell that has xylose isomerase activity following the teachings above. In one embodiment a heterologous nucleic acid molecule encoding a polypeptide having xylose isomerase activity and amino acid sequence with at least 85% sequence identity to any of the amino acid sequences of SEQ ID NO:1, 3, 5, or 7 is introduced into a yeast strain. In various embodiments the amino acid sequence of the polypeptide has at least about 85%, 86%, 87%, 88%, 89%, 90%, 91%, 92%, 93%, 94%, 95%, 96%, 97%, 98%, 99% or up to 100% to any of SEQ ID NO:1, 3, 5, and 7.

In one embodiment the introduced nucleic acid molecule is a part of a chimeric gene that is introduced into a yeast cell for expression, as described above.

In one embodiment the described nucleic acid molecule is introduced into a yeast cell which has other genetic modifications providing a complete xylose utilization pathway, once the xylose isomerase activity is introduced, as described above for the yeast host cell. Introduction of xylose isomerase activity and the additional genetic modifications may be performed in any order, and/or with two or more of introduction/modification performed concurrently. These cells are able to grow in medium containing xylose as the sole carbon source. More typically, these cells are grown in medium containing xylose as well as other sugars such as glucose and arabinose. This allows effective use of the sugars found in a hydrolysate medium that is prepared from cellulosic biomass by pretreatment and saccharification.

In further embodiments the described nucleic acid molecule is introduced into a yeast cell which has a metabolic pathway that produces a target chemical. Introduction of xylose isomerase activity and the metabolic pathway may be performed in any order, and/or with two or more genetic modifications performed concurrently. Examples of target compounds include ethanol, butanol, and 1,3-propanediol. Yeast cells containing metabolic pathways for production of target chemicals are described above.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

The meaning of abbreviations is as follows: "kb" means kilobase(s), "bp" means base pairs, "nt" means nucleotide(s), "hr" means hour(s), "min" means minute(s), "sec" means second(s), "d" means day(s), "L" means liter(s), "ml" or "mL" means milliliter(s), "µL" means microliter(s), "µg" means microgram(s), "ng" means nanogram(s), "mg" means milligram(s), "mM" means millimolar, "µM" means micromolar, "nm" means nanometer(s), "µmol" means micromole(s), "pmol" means picomole(s), "XI" is xylose isomerase, "nt" means nucleotide.

Standard recombinant DNA and molecular cloning techniques used here are well known in the art and are described by Sambrook, J., Fritsch, E. F. and Maniatis, T., *Molecular Cloning: A Laboratory Manual*, 2$^{nd}$ ed., Cold Spring Harbor Laboratory: Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience, Hoboken, N.J. (1987), and by *Methods in Yeast Genetics*, 2005, Cold Spring Harbor Laboratory Press, Cold Spring Harbor, N.Y.

HPLC Analysis

Cell culture samples were taken at timed intervals and analyzed for EtOH and xylose using either a Waters HPLC system (Alliance system, Waters Corp., Milford, Mass.) or an Agilent 1100 Series LC; conditions=0.6 mL/min of 0.01 N $H_2SO_4$, injection volume=10 µL, autosampler temperature=10° C., column temperature=65° C., run time=25 min, detection by refractive index (maintained at 40° C.). The HPLC column was purchased from BioRad (Aminex HPX-87H, BioRad Inc., Hercules, Calif.). Analytes were quantified by refractive index detection and compared to known standards.

Example 1

Up-Regulation of the Native Pentose Pathway in *S. cerevisiae*

In addition to expression of an active xylose isomerase enzyme, a robust pentose pathway is necessary for efficient use of xylose and ethanol production under oxygen-limiting conditions in *S. cerevisiae*. The pentose pathway consists of five enzymes. In *S. cerevisiae*, these proteins are xylulokinase (XKS1), transaldolase (TAL1), transketolase 1 (TKL1), D-ribulose-5-phosphate 3-epimerase (RPE1), and ribose 5-phosphate ketol-isomerase (RKI1). In order to increase the expression of these proteins, their coding regions from the *S. cerevisiae* genome were cloned for expression under different promoters and integrated in the *S. cerevisiae* chromosome. The GRE3 locus encoding aldose reductase was chosen for integration. To construct such this strain, the first step was the construction of an integration vector called P5 Integration Vector in GRE3.

The sequence of the P5 Integration Vector in GRE3 is given as SEQ ID NO:18, and the following numbers refer to nucleotide positions in this vector sequence. Gaps between the given nt numbers include sequence regions containing restriction sites. The TAL1 coding region (15210 to 16217) was expressed with the TPI1 promoter (14615 to 15197) and uses the TAL1 t terminator. The RPE1 (13893 to 14609) coding region was expressed with the FBA1 promoter (13290 to 13879) and uses the terminator at the upstream end of the TPI1 promoter. RKI1 coding region (nt 11907 to 12680) was expressed with the TDH3 promoter (11229 to 11900) and uses the GPDt (previously called TDH3t) terminator. The TKL1 coding region (nt 8830 to 10872) was expressed with the PGK1 promoter (nt 8018 to 8817) and uses the TKL1t terminator. The XKS1 coding region (nt 7297 to 5495 to) was expressed with the Ilv5 promoter (nt 8009 to 7310) and uses the ADH terminator. In this integration vector, the URA3 marker (nt 332 to 1135) was flanked by loxP sites (nt 42 to 75 and nt 1513 to 1546) for recycling of the marker. The vector contains integration arms for the GRE3 locus (nt 1549 to 2089 and nt 4566 to 5137). This P5 Integration Vector in GRE3 can be linearized by digesting with the KasI enzyme before integration.

The yeast strain chosen for this study was BP1548 which is a haploid strain derived from prototrophic diploid strain CBS 8272 (Centraalbureau voor Schimmelcultures (CBS) Fungal Biodiversity Centre, Netherlands). This strain is in the CEN.PK lineage of *Saccharomyces cerevisiae* strains. BP1548 contains the MATα mating type and deletions of the URA3 and HIS3 genes.

To produce BP1548, first CBS 8272 was sporulated and a tetrad was dissected to yield four haploid strains using standard procedures (Amberg et al., Methods in Yeast Genetics, 2005). One of the MATα haploids, PNY0899, was selected for further modifications. The URA3 coding sequence (ATG through stop codon) and 130 bp of sequence upstream of the URA3 coding sequence was deleted by homologous recombination using a KanMX deletion cassette flanked by loxP sites, primer binding sites, and homologous sequences outside of the URA3 region to be deleted. After removal of the KanMX marker using the cre recombinase, a 95 bp sequence consisting of a loxP site flanked by the primer binding sites remained as a URA3 deletion scar in the genome (SEQ ID NO:19). This sequence is located in the genome between URA3 upstream sequence (SEQ ID NO:20) and URA3 downstream sequence (SEQ ID NO:21). The HIS3 coding sequence (ATG up to the stop codon) was deleted by homologous recombination using a scarless method. The deletion joins genomic sequences that were originally upstream (SEQ ID NO:22) and downstream (SEQ ID NO:23) of the HIS3 coding sequence. The KasI integration fragment containing all five pentose pathway genes in vector P5 Integration Vector in GRE3 was transformed into the BP1548 strain using the Frozen-EZ Yeast Transformation II Kit from Zymo Research (Irvine, Calif.). Transformants were selected on synthetic dropout (SD) medium lacking uracil. To recycle the URA3 marker, the CRE recombinase vector pJT254 (SEQ ID NO:24) was transformed into these integrated strains. This vector was derived from pRS413 and the cre coding region (nt 2562 to 3593) was under the control of the GAL1 promoter (nt 2119 to 2561). Strains that could no longer grow on SD (-uracil) medium were selected. Further passages on YPD medium was used to cure the plasmid pJT257. The resulting strain was designated as C52-79.

Example 2

Selection and Expression of Bacterial Xylose Isomerases

In order to identify candidate bacterial xylose isomerases that may be active when expressed in yeast, we used amino acid sequences of the xylose isomerases from *Ruminococcus flavefaciens* FD-1 (SEQ ID NO:11) and from *Ruminococcus champanellensis* 18P13 (SEQ ID NO:9) in a BLAST search against the GenBank database (National Center for Biotechnology Information (NCBI); Benson et al. Nucleic Acids Research, 2011 January; 39 (Database issue):D32-7). From this search, six bacterial xylose isomerases were chosen for testing based on sequence identity. These were the putative xylose isomerases from *Lachnospiraceae bacterium* ICM7 (SEQ ID NO:1), *Lachnospiraceae bacterium* oral taxon 107 str. F0167 (SEQ ID NO:3), *Lachnospiraceae bacterium* oral taxon 082 str. F0431 (SEQ ID NO:5), *Eubacterium saburreum* DSM 3986 (SEQ ID NO:7), *Leptotrichia goodfellowii* F0264 (SEQ ID NO:13), and *Sebaldella termitidis* ATCC 33387 (SEQ ID NO:15). DNA sequences encoding these proteins were synthesized using codon optimization for expression in *S. cerevisiae* and were designated as xylA (Hm1) (SEQ ID NO:2), xylA(Hm2) (SEQ ID NO:4), xylA (Hm3) (SEQ ID NO:6), xylA(Hm4) (SEQ ID NO:8), xylA (Oral-2) (SEQ ID NO:14), and xylA(Term1) (SEQ ID NO:X16), respectively. In addition, a codon-optimized coding region for the *Ruminococcus champanellensis* 18P13 xylose isomerase was synthesized and named xylA-10 (SEQ ID NO:10).

The synthesized xylA coding regions were expressed using a 1,184-nt promoter of the *S. cerevisiae* acetohydroxyacid reductoisomerase gene (ILV5p) and a 635-nt terminator of the *S. cerevisiae* acetohydroxyacid reductoisomerase gene (ILV5t). The chimeric genes were located between NotI and XhoI sites in a pHR81-based shuttle vector, with the coding region between PmeI and SfiI sites. The pHR81 vector (ATCC #87541) contains a pMB1 origin and an ampicillin resistance (ampR) marker to allow plasmid propagation and selection, respectively, in *E. coli*. In addition, pHR81 has a 2 micron replication origin, a URA3 selection marker, and LEU 2-d for propagation and selection in yeast, which gives high copy number in *S. cerevisiae* when grown in medium lacking leucine, The sequence of the pHR81 vector containing the ILVp-xylA(Hm1)-ILV5t chimeric gene is SEQ ID NO:17. Vectors containing the other coding regions are identical with the exception of the substitution of each separate coding region between ILV5p and ILV5t, between PmeI and SfiI sites. The xylA(Hm1) vector was named pHR81 ilv5p xylA (Hm1), with other vectors having the same name, except substituting the specific xylA coding region designation. These constructs were transformed into the C52-79 strain (Example 1) and transformants were selected on plates containing synthetic glucose medium lacking uracil: 6.7 g/L yeast nitrogen base without amino acids (Amresco, Solon, Ohio), 0.77 g/L minus ura Drop Out supplement (Clontech Laboratories, Mountain View, Calif.), 20 g/L glucose. Transformants were then tested for growth and ethanol production.

Example 3

Growth and Ethanol Production in *S. cerevisiae* Containing Different Bacterial Xylose Isomerases

*S. cerevisiae* strain C52-79 (Example 1) lacks the ability to use xylose as the energy and carbon source since it lacks xylose isomerase activity. Yeast strains expressing xylA (Hm1), xylA (Hm2), xylA(Hm3), xylA(Hm4), xylA(Oral-2), xylA(Term1), and xylA-10 chimeric genes were tested in YPX medium (10 g/l yeast extract, 20 g/l peptone, and 40 g/l of xylose). To perform this test, strains were inoculated into 10 ml of YPX medium in 50 ml tissue culture tubes at a starting $OD_{600}$ of 0.5. The lids were tightly closed and the tubes were placed in a 30° C. rotary shaker set at a speed of 225 rpm. At different time intervals (24 hr, 44 hr, and 72 hr), samples were taken and the xylose and ethanol concentrations were determined by HPLC analysis as described in General Methods, as well as recording the $OD_{600}$. Three individual cultures for each strain were grown and analyzed. The results were averaged for each set of 3 replicates. Strains with xylA(Hm1), xylA(Oral-2), xylA(Term-1), and xylA-10 were assayed at the same time. Strains with xylA(Hm2) and xylA(Hm3) were assayed at the same time. The strain with xylA(Hm4) was assayed separately. All of the results are given in Table 3.

TABLE 3

Growth, xylose consumption, and ethanol production of yeast strains expressing various xylose isomerases

| Vector in Strain | $OD_{600}$ Av. | SD | Xylose consumed (g/L) Av. | SD | Ethanol Produced (g/L) Av. | SD |
|---|---|---|---|---|---|---|
| After 24 hours | | | | | | |
| pHR81 ilv5p xylA(Hm1) | 11.85 | 0.40 | 33.86 | 0.70 | 13.07 | 0.29 |
| pHR81 ilv5p xylA(Hm2) | 11.60 | 0.36 | 32.08 | 2.34 | 12.56 | 0.82 |
| pHR81 ilv5p xylA(Hm3) | 10.36 | 0.20 | 24.25 | 1.33 | 9.51 | 0.60 |
| pHR81 ilv5p xylA(Hm4) | 6.54 | 0.30 | 7.65 | 0.72 | 2.57 | 0.30 |
| pHR81 ilv5p xylA(Oral-2) | 2.88 | 0.09 | 0.52 | 0.08 | 0.00 | 0.00 |
| pHR81 ilv5p xylA(Term-1) | 2.35 | 0.56 | 0.47 | 0.07 | 0.00 | 0.00 |
| pHR81 ilv5p xylA(xylA-10) | 3.00 | 0.41 | 0.40 | 0.13 | 0.00 | 0.00 |
| After 44 hours | | | | | | |
| pHR81 ilv5p xylA(Hm1) | 12.79 | 0.51 | 40.00 | 0.00 | 15.82 | 0.11 |
| pHR81 ilv5p xylA(Hm2) | 13.07 | 0.21 | 39.92 | 0.00 | 15.17 | 0.33 |
| pHR81 ilv5p xylA(Hm3) | 12.48 | 0.26 | 39.92 | 0.00 | 16.20 | 0.18 |
| pHR81 ilv5p xylA(Hm4) | 11.26 | 0.84 | 31.50 | 2.67 | 11.65 | 1.20 |
| pHR81 ilv5p xylA(Oral-2) | 2.88 | 0.09 | 0.60 | 0.15 | 0.00 | 0.00 |
| pHR81 ilv5p xylA(Term-1) | 2.78 | 0.29 | 0.04 | 0.09 | 0.00 | 0.00 |
| pHR81 ilv5p xylA(xylA10) | 3.22 | 0.50 | 0.64 | 0.12 | 0.00 | 0.00 |
| After 72 hours | | | | | | |
| pHR81 ilv5p xylA(Oral-2) | 2.70 | 0.35 | 0.71 | 0.24 | 0.00 | 0.00 |
| pHR81 ilv5p xylA(Term-1) | 2.61 | 0.17 | 1.20 | 0.06 | 0.00 | 0.00 |
| pHR81 ilv5p xylA(xylA-10) | 3.02 | 0.13 | 1.00 | 0.10 | 0.00 | 0.00 |

As shown in Table 3, yeast strains containing the chimeric gene for expression of Hm1, Hm2, Hm3, and Hm4 consumed xylose and at the same time, produced ethanol when measured at 24 hours. After 44 hours of incubation essentially all of the xylose was consumed and over 15 g/L of ethanol was produced by strains expressing Hm1, Hm2, and Hm3. For strains expressing Hm4, a majority of the xylose was consumed after 44 hours, producing about 11 g/L of ethanol. These results indicate that Hm1, Hm2, Hm3, and Hm4 were expressed as active xylose isomerase enzymes in *S. cerevisiae*. Strains expressing other Oral-2, Term-1, and XylA10, however, consumed almost no xylose and did not produce ethanol even after 72 hours.

What is claimed is:

1. A recombinant yeast cell comprising a complete xylose utilization pathway including a codon optimized heterologous nucleic acid molecule encoding a polypeptide comprising SEQ ID NO:7, wherein the codon optimization is for expression in a yeast cell, wherein the codon optimized heterologous nucleic acid molecule includes an operably linked promoter and is expressed producing xylose isomerase activity in the yeast cell, and wherein the heterologous nucleic acid molecule is chimeric.

2. The recombinant yeast cell of claim 1, further having the ability to grow on xylose as a sole carbon source.

3. The recombinant yeast cell of claim 2, further comprising a metabolic pathway that produces a target compound.

4. The recombinant yeast cell of claim 3, wherein the target compound is selected from the group consisting of ethanol, butanol, and 1,3-propanediol.

5. The recombinant yeast cell of claim 3, wherein the target compound is ethanol.

6. The recombinant yeast cell of claim 5, wherein the metabolic pathway that produces the target compound comprises genes encoding the following enzymes: xylulokinase, transaldolase, transketolase 1, D-ribulose-5-phosphate 3-epimerase, and ribose 5-phosphate ketol-isomerase.

7. The recombinant yeast cell of claim 1, wherein the yeast cell is of the genus *Kluyveromyces, Candida, Pichia, Hansenula, Schizosaccharomyces, Kloeckera, Schwanniomyces, Yarrowia,* or *Saccharomyces*.

8. The recombinant yeast cell of claim 7, wherein the yeast cell is of the genus *Saccharomyces*.

9. The recombinant yeast cell of claim 8, wherein the yeast cell is *Saccharomyces cerevisiae*.

* * * * *

SEQUENCE LISTING

```
<160> NUMBER OF SEQ ID NOS: 24

<210> SEQ ID NO 1
<211> LENGTH: 442
<212> TYPE: PRT
<213> ORGANISM: Lachnospiraceae bacterium

<400> SEQUENCE: 1

Met Lys Glu Phe Phe Pro Ser Ile Ser Pro Ile Lys Phe Glu Gly Ser
1               5                   10                  15

Glu Ser Lys Asn Pro Leu Ser Phe Lys Tyr Tyr Asp Ala Lys Arg Val
                20                  25                  30

Ile Met Gly Lys Thr Met Glu Glu His Leu Ser Phe Ala Met Ala Trp
            35                  40                  45

Trp His Asn Leu Cys Ala Ser Gly Val Asp Met Phe Gly Gln Gly Thr
        50                  55                  60

Ala Asp Lys Gly Phe Gly Glu Asn Leu Gly Thr Met Glu His Ala Lys
65                  70                  75                  80

Ala Lys Val Asp Ala Gly Ile Glu Phe Met Gln Lys Leu Gly Ile Lys
                85                  90                  95

Tyr Tyr Cys Phe His Asp Thr Asp Ile Val Pro Glu Asp Gln Glu Asp
                100                 105                 110

Ile Asn Val Thr Asn Ala Arg Leu Asp Glu Ile Thr Asp Tyr Ile Leu
            115                 120                 125
```

Glu Lys Thr Lys Gly Thr Asp Ile Lys Cys Leu Trp Ala Thr Cys Asn
    130                 135                 140

Met Phe Ser Asn Pro Arg Phe Met Asn Gly Ala Gly Ser Ser Asn Ser
145                 150                 155                 160

Ala Asp Val Phe Cys Phe Ala Ala Gln Ala Lys Lys Gly Leu Glu
            165                 170                 175

Asn Ala Val Lys Leu Gly Ala Lys Gly Phe Val Phe Trp Gly Arg
            180                 185                 190

Glu Gly Tyr Glu Thr Leu Leu Asn Thr Asp Met Lys Leu Glu Glu Glu
        195                 200                 205

Asn Ile Ala Thr Leu Phe Thr Met Cys Arg Asp Tyr Gly Arg Ser Ile
    210                 215                 220

Gly Phe Lys Gly Asp Phe Tyr Ile Glu Pro Lys Pro Lys Glu Pro Met
225                 230                 235                 240

Lys His Gln Tyr Asp Phe Asp Ala Ala Thr Ala Ile Gly Phe Leu Arg
            245                 250                 255

Lys Tyr Gly Leu Asp Lys Asp Phe Lys Met Asn Ile Glu Ala Asn His
        260                 265                 270

Ala Thr Leu Ala Gly His Thr Phe Gln His Glu Leu Arg Val Ser Ala
    275                 280                 285

Ile Asn Gly Met Leu Gly Ser Val Asp Ala Asn Gln Gly Asp Thr Leu
290                 295                 300

Leu Gly Trp Asp Thr Asp Gln Phe Pro Thr Asn Val Tyr Asp Thr Thr
305                 310                 315                 320

Leu Ala Met Tyr Glu Ile Leu Lys Ala Gly Gly Leu Ser Gly Gly Leu
            325                 330                 335

Asn Phe Asp Ser Lys Asn Arg Arg Pro Ser Asn Thr Ala Glu Asp Met
        340                 345                 350

Phe Tyr Gly Phe Ile Ala Gly Met Asp Thr Phe Ala Leu Gly Leu Ile
    355                 360                 365

Lys Ala Ala Gln Ile Ile Glu Asp Gly Arg Ile Asp Glu Phe Val Lys
    370                 375                 380

Glu Arg Tyr Ser Ser Tyr Asn Ser Gly Ile Gly Glu Lys Ile Arg Asn
385                 390                 395                 400

Arg Ser Val Thr Leu Val Glu Cys Ala Glu Tyr Ala Leu Lys Met Lys
            405                 410                 415

Lys Pro Glu Leu Pro Glu Ser Gly Arg Gln Gly Tyr Leu Glu Thr Val
        420                 425                 430

Val Asn Asn Ile Phe Phe Asn Ser Lys Leu
    435                 440

<210> SEQ ID NO 2
<211> LENGTH: 1326
<212> TYPE: DNA
<213> ORGANISM: artificial sequence
<220> FEATURE:
<223> OTHER INFORMATION: coding region for Hm1 optimized for expression
      in Saccharomyces cerevisiae

<400> SEQUENCE: 2
atgaaggagt tcttcccatc catctctcca atcaagttcg aaggttccga atccaagaac    60
ccattgtctt tcaagtacta cgacgctaag agagttatca tgggtaaaac catggaagaa   120
cacttgtctt tcgctatggc ttggtggcac aacttgtgtg cttccggtgt tgacatgttc   180
ggtcaaggta ctgctgacaa gggtttcggt gaaaacttgg gtactatgga aacacgctaag  240

```
gctaaggttg acgctggtat cgagttcatg caaaagttgg gtatcaagta ctactgtttc    300
cacgacaccg atatcgttcc agaagaccaa gaagatatca acgtcaccaa cgctagattg    360
gacgaaatca ctgattacat cttggaaaag accaagggta ctgacatcaa gtgtttgtgg    420
gctacttgta acatgttctc taacccaaga ttcatgaacg gtgctggttc ttctaactct    480
gctgacgttt tctgtttcgc tgctgctcaa gctaagaagg gtttggaaaa cgctgttaag    540
ttgggtgcta agggtttcgt cttctggggt ggtagagaag ttacgaaaac cttgttgaac    600
actgacatga agttggaaga agaaaacatc gctaccttgt tcactatgtg tagagactac    660
ggtagatcta tcggtttcaa gggtgacttc tacatcgaac caaagccaaa ggaaccaatg    720
aagcaccaat acgacttcga tgctgctacc gctatcggtt tcttgagaaa gtacggtttg    780
gacaaggatt tcaagatgaa catcgaagct aaccacgcta ccttggctgg tcacactttc    840
caacacgaat tgagagtttc tgctatcaac ggtatgttgg ttccgttga cgctaaccaa    900 ggtgacactt tgttgggttg ggacaccgat caattcccaa ctaacgttta cgacaccact    960
ttggctatgt acgaaatctt gaaggctggt ggtttgtctg gtggtttgaa cttcgactct   1020
aagaacagaa gaccatccaa caccgctgaa gacatgttct acggtttcat cgctggtatg   1080
gacactttcg ctttgggttt gatcaaggct gctcaaatca tcgaagacgg tagaatcgat   1140
gaatttgtca ggaaagata ctcttcctac aactctggta tcggtgaaaa gatcagaaac   1200
agatccgtta ctttggtcga atgtgctgaa tacgctttga agatgaagaa gccagaattg   1260
ccagaatctg gtagacaaga atacttggaa accgtcgtca acaacatctt cttcaactct   1320
aagttg                                                               1326
```

<210> SEQ ID NO 3
<211> LENGTH: 442
<212> TYPE: PRT
<213> ORGANISM: Lachnospiraceae bacterium

<400> SEQUENCE: 3

```
Met Lys Glu Phe Phe Pro Gly Ile Ser Pro Val Lys Phe Glu Gly Ser
1               5                   10                  15

Glu Ser Lys Asn Pro Leu Ser Phe Lys Tyr Tyr Asp Ala Lys Arg Val
            20                  25                  30

Ile Met Gly Lys Thr Met Glu Glu His Leu Ser Phe Ala Met Ala Trp
        35                  40                  45

Trp His Asn Leu Cys Ala Ser Gly Val Asp Met Phe Gly Gln Gly Thr
    50                  55                  60

Ala Asp Lys Gly Phe Gly Glu Ser Ser Gly Thr Met Gly His Ala Lys
65                  70                  75                  80

Ala Lys Val Asp Ala Gly Ile Glu Phe Met Lys Lys Leu Gly Ile Lys
                85                  90                  95

Tyr Tyr Cys Phe His Asp Thr Asp Ile Val Pro Glu Asp Gln Glu Asp
            100                 105                 110

Ile Asn Val Thr Asn Ala Arg Leu Asp Glu Ile Thr Asp Tyr Ile Leu
        115                 120                 125

Glu Lys Thr Lys Gly Ser Asp Ile Lys Cys Leu Trp Thr Thr Cys Asn
    130                 135                 140

Met Phe Gly Asn Pro Arg Phe Met Asn Gly Ala Gly Ser Ser Asn Ser
145                 150                 155                 160

Ala Asp Val Phe Cys Phe Ala Ala Ala Gln Ala Lys Lys Gly Leu Glu
                165                 170                 175
```

```
Asn Ala Val Lys Leu Gly Ala Lys Gly Phe Val Phe Trp Gly Gly Arg
            180                 185                 190
Glu Gly Tyr Glu Thr Leu Leu Asn Thr Asp Met Lys Leu Glu Glu Glu
        195                 200                 205
Asn Ile Ala Thr Leu Phe Thr Met Cys Arg Asp Tyr Gly Arg Ser Ile
    210                 215                 220
Gly Phe Lys Gly Asp Phe Tyr Ile Glu Pro Lys Pro Lys Glu Pro Met
225                 230                 235                 240
Lys His Gln Tyr Asp Phe Asp Ala Ala Thr Ala Ile Gly Phe Leu Arg
                245                 250                 255
Lys Tyr Gly Leu Asp Lys Asp Phe Lys Leu Asn Ile Glu Ala Asn His
            260                 265                 270
Ala Thr Leu Ala Gly His Thr Phe Gln His Glu Leu Arg Val Ser Ala
        275                 280                 285
Ile Asn Gly Met Leu Gly Ser Val Asp Ala Asn Gln Gly Asp Thr Leu
    290                 295                 300
Leu Gly Trp Asp Thr Asp Gln Phe Pro Thr Asn Ile Tyr Asp Thr Thr
305                 310                 315                 320
Phe Ala Met Tyr Glu Ile Leu Lys Ala Gly Gly Leu Ser Gly Gly Leu
                325                 330                 335
Asn Phe Asp Ser Lys Asn Arg Arg Pro Ser Asn Thr Ala Glu Asp Met
            340                 345                 350
Phe Tyr Gly Phe Ile Ala Gly Met Asp Thr Phe Ala Leu Gly Leu Ile
        355                 360                 365
Lys Ala Ala Gln Ile Ile Glu Asp Gly Arg Ile Asp Glu Phe Ile Lys
    370                 375                 380
Glu Arg Tyr Ser Ser Tyr Ser Thr Gly Ile Gly Glu Lys Ile Arg Asn
385                 390                 395                 400
Lys Ser Val Thr Leu Glu Glu Cys Ala Glu Tyr Ala Ala Lys Leu Lys
                405                 410                 415
Lys Pro Glu Leu Pro Glu Ser Gly Arg Gln Glu Tyr Leu Glu Thr Val
            420                 425                 430
Val Asn Asn Ile Leu Phe Asn Ser Lys Leu
        435                 440

<210> SEQ ID NO 4
<211> LENGTH: 1326
<212> TYPE: DNA
<213> ORGANISM: artificial sequence
<220> FEATURE:
<223> OTHER INFORMATION: coding region for L. bacterium oral taxon 107
      xylose isomerase optimized for expression in S. cerevisiae

<400> SEQUENCE: 4
atgaaggagt tcttcccagg tatctctcca gtcaagttcg aaggttctga atccaagaac      60
ccattgtctt tcaagtacta cgatgctaag agagttatca tgggtaaaac catggaagaa    120
cacttgtctt tcgctatggc ttggtggcac aacttgtgtg cttccggtgt tgacatgttc    180
ggtcaaggta ctgctgacaa gggtttcggt gaatcttccg gtactatggg tcacgctaag    240
gctaaggttg acgctggtat cgagttcatg aagaagttgg gtatcaagta ctactgtttc    300
cacgacaccg atatcgttcc agaagaccaa gaagatatca cgtcactaa cgctagattg    360 gacgaaatca ccgattacat cttggaaaag actaagggtt ctgacatcaa gtgtttgtgg    420
accacttgta acatgttcgg taacccaaga ttcatgaacg gtgctggttc ttctaactct    480
```

```
gctgacgttt tctgtttcgc tgctgctcaa gctaagaagg gtttggaaaa cgctgttaag      540
ttgggtgcta agggtttcgt cttctggggt ggtagagaag gttacgaaac cttgttgaac      600
actgacatga agttggaaga agaaaacatc gctaccttgt tcactatgtg tagagactac      660
ggtagatcta tcggtttcaa gggtgacttc tacatcgaac caaagccaaa ggaaccaatg      720
aagcaccaat acgacttcga tgctgctacc gctatcggtt tcttgagaaa gtacggtttg      780
gacaaggatt tcaagttgaa catcgaagct aaccacgcta ccttggctgg tcacactttc      840
caacacgaat tgagagtttc tgctatcaac ggtatgttgg gttccgttga cgctaaccaa      900
ggtgacactt tgttgggttg ggacaccgat caattcccaa ctaacatcta cgacaccact      960
ttcgctatgt acgaaatctt gaaggctggt ggtttgtctg gtggtttgaa cttcgactct     1020
aagaacagaa gaccatccaa caccgctgaa gacatgttct acggtttcat cgctggtatg     1080
gacactttcg ctttgggttt gatcaaggct gctcaaatca tcgaagacgg tagaatcgat     1140
gagttcatca aggaaagata ctcttcctac tctaccggta tcggtgaaaa gatcagaaac     1200
aagtccgtta ctttggaaga atgtgctgaa tacgctgcta agttgaagaa gccagaattg     1260
ccagaatctg gtagacaaga atacttggaa accgtcgtca acaacatctt gttcaactct     1320
aagttg                                                                1326
```

<210> SEQ ID NO 5  
<211> LENGTH: 439  
<212> TYPE: PRT  
<213> ORGANISM: Lachnospiraceae bacterium

<400> SEQUENCE: 5

```
Met Lys Glu Phe Phe Pro Gly Ile Ser Pro Val Lys Phe Glu Gly Lys
1               5                   10                  15

Asp Ser Lys Asn Pro Leu Ser Phe Lys Tyr Tyr Asp Ala Lys Arg Val
            20                  25                  30

Ile Met Gly Lys Thr Met Glu Glu His Leu Ser Phe Ala Met Ala Trp
        35                  40                  45

Trp His Asn Leu Cys Ala Cys Gly Val Asp Met Phe Gly Gln Gly Thr
    50                  55                  60

Ile Asp Lys Ser Phe Gly Ala Leu Pro Gly Thr Met Glu His Ala Lys
65                  70                  75                  80

Ala Lys Val Asp Ala Gly Ile Glu Phe Met Gln Lys Leu Gly Ile Lys
                85                  90                  95

Tyr Tyr Cys Phe His Asp Thr Asp Ile Val Pro Glu Asp Gln Glu Asp
            100                 105                 110

Ile Asn Val Thr Asn Ala Arg Leu Asp Glu Ile Thr Asp Tyr Ile Leu
        115                 120                 125

Glu Lys Thr Lys Gly Thr Asp Ile Lys Cys Leu Trp Thr Thr Cys Asn
    130                 135                 140

Met Phe Ser Asn Pro Arg Phe Met Asn Gly Ala Gly Ser Ser Asn Ser
145                 150                 155                 160

Ala Asp Val Phe Cys Phe Ala Ala Ala Gln Ala Lys Lys Gly Leu Glu
                165                 170                 175

Asn Ala Val Lys Leu Gly Ala Lys Gly Phe Val Phe Trp Gly Gly Arg
            180                 185                 190

Glu Gly Tyr Glu Thr Leu Leu Asn Thr Asp Met Lys Leu Glu Glu Glu
        195                 200                 205

Asn Ile Ala Thr Leu Phe Thr Met Cys Arg Asp Tyr Gly Arg Ser Ile
    210                 215                 220
```

```
Gly Phe Met Gly Asp Phe Tyr Ile Glu Pro Lys Pro Lys Glu Pro Met
225                 230                 235                 240

Lys His Gln Tyr Asp Phe Asp Ala Ala Thr Ala Ile Gly Phe Leu Arg
                245                 250                 255

Lys Tyr Gly Leu Glu Lys Asp Phe Lys Met Asn Ile Glu Ala Asn His
            260                 265                 270

Ala Thr Leu Ala Gly His Thr Phe Gln His Glu Leu Arg Val Cys Ala
        275                 280                 285

Val Asn Gly Met Ile Gly Ser Val Asp Ala Asn Gln Gly Asp Thr Leu
    290                 295                 300

Leu Gly Trp Asp Thr Asp Gln Phe Pro Thr Asn Val Tyr Asp Thr Thr
305                 310                 315                 320

Leu Ala Met Tyr Glu Ile Leu Lys Ala Gly Gly Leu Arg Gly Gly Leu
                325                 330                 335

Asn Phe Asp Ser Lys Asn Arg Arg Pro Ser Asn Thr Ala Asp Asp Met
            340                 345                 350

Phe Tyr Gly Phe Ile Ala Gly Met Asp Ala Phe Ala Leu Gly Leu Ile
        355                 360                 365

Lys Ala Ala Glu Ile Ile Glu Asp Gly Arg Ile Asp Glu Phe Val Lys
    370                 375                 380

Glu Arg Tyr Ser Ser Tyr Asn Ser Gly Ile Gly Glu Lys Ile Arg Asn
385                 390                 395                 400

Arg Ala Val Thr Leu Val Glu Cys Ala Glu Tyr Ala Ala Lys Leu Lys
                405                 410                 415

Lys Pro Glu Leu Pro Asp Ser Gly Lys Gln Glu Tyr Leu Glu Ser Val
            420                 425                 430

Val Asn Asn Ile Leu Phe Gly
        435

<210> SEQ ID NO 6
<211> LENGTH: 1317
<212> TYPE: DNA
<213> ORGANISM: artificial sequence
<220> FEATURE:
<223> OTHER INFORMATION: coding region for L. bacterium oral taxon 082
      xylose isomerase optimized for expression in S. cerevisiae

<400> SEQUENCE: 6
atgaaggagt tcttcccagg tatctcccca gtcaagttcg aaggcaagga ctccaagaac       60
ccattgtctt tcaagtacta cgatgctaag agagttatca tgggtaaaac catggaagaa      120
cacttgtctt tcgctatggc ttggtggcac aacttgtgtg cttgtggtgt tgacatgttc      180
ggtcaaggta ctatcgataa gtccttcggt gctttgccag gtactatgga acacgctaag      240
gctaaggttg acgctggtat cgagttcatg caaaagttgg gtatcaagta ctactgtttc      300
cacgacactg atatcgttcc agaagaccaa gaagatatca acgtcaccaa cgctagattg      360
gacgaaatca ctgattacat cttggaaaag accaagggta ctgacatcaa gtgtttgtgg      420
accacttgta acatgttctc taacccaaga ttcatgaacg gtgctggttc ttctaactct      480
gctgacgttt ctgtttcgc tgctgctcaa gctaagaagg gtttggaaaa cgctgttaag      540
ttgggtgcta agggtttcgt cttctggggt ggtagagaag gttacgaaac cttgttgaac      600
actgacatga gttggaaga gaaaacatc gctaccttgt tcactatgtg tagagactac      660
ggtagatcta tcggtttcat gggtgacttc tacatcgaac caaagccaaa ggaaccaatg      720
aagcaccaat acgacttcga tgctgctacc gctatcggtt tcttgagaaa gtacggtttg      780
```

-continued

```
gaaaaggact tcaagatgaa catcgaagct aaccacgcta ccttggctgg tcacactttc    840
caacacgaat tgagagtttg tgctgtcaac ggtatgatcg ttctgttga cgctaaccaa     900 ggtgacacct tgttgggttg ggacaccgat caattcccaa ctaacgtcta cgacaccact    960
ttggctatgt acgaaatctt gaaggctggt ggtttgagag tggtttgaa cttcgactct    1020 aagaacagaa gaccatccaa cactgctgac gatatgttct acggtttcat cgctggtatg   1080
gacgctttcg ctttgggttt gatcaaggct gctgaaatca tcgaagacgg tagaatcgat   1140
gaatttgtta aggaaagata ctcttcctac aactctggta tcggtgaaaa gatcagaaac   1200
agagctgtta ctttggtcga atgtgctgaa tacgctgcta agttgaagaa gccagaattg   1260
ccagactccg gcaagcaaga atacttggaa tccgtcgtca caacatcttt gttcggt     1317
```

<210> SEQ ID NO 7
<211> LENGTH: 457
<212> TYPE: PRT
<213> ORGANISM: Eubacterium saburreum

<400> SEQUENCE: 7

```
Met Lys Thr Lys Asn Asn Ile Ile Cys Thr Ile Ala Leu Lys Gly Asp
1               5                   10                  15

Ile Phe Met Lys Glu Phe Phe Pro Gly Ile Ser Pro Val Lys Phe Glu
            20                  25                  30

Gly Arg Asp Ser Lys Asn Pro Leu Ser Phe Lys Tyr Tyr Asp Ala Lys
        35                  40                  45

Arg Val Ile Met Gly Lys Thr Met Glu Glu His Leu Ser Phe Ala Met
    50                  55                  60

Ala Trp Trp His Asn Leu Cys Ala Cys Gly Val Asp Met Phe Gly Gln
65                  70                  75                  80

Gly Thr Val Asp Lys Ser Phe Gly Glu Ser Gly Thr Met Glu His
                85                  90                  95

Ala Arg Ala Lys Val Asp Ala Gly Ile Glu Phe Met Lys Lys Leu Gly
            100                 105                 110

Ile Lys Tyr Tyr Cys Phe His Asp Thr Asp Ile Val Pro Glu Asp Gln
        115                 120                 125

Glu Asp Ile Asn Val Thr Asn Ala Arg Leu Asp Glu Ile Thr Asp Tyr
    130                 135                 140

Ile Leu Glu Lys Thr Lys Asp Thr Asp Ile Lys Cys Leu Trp Thr Thr
145                 150                 155                 160

Cys Asn Met Phe Ser Asn Pro Arg Phe Met Asn Gly Ala Gly Ser Ser
                165                 170                 175

Asn Ser Ala Asp Val Phe Cys Phe Ala Ala Ala Gln Ala Lys Lys Gly
            180                 185                 190

Leu Glu Asn Ala Val Lys Leu Gly Ala Lys Gly Phe Val Phe Trp Gly
        195                 200                 205

Gly Arg Glu Gly Tyr Glu Thr Leu Leu Asn Thr Asp Met Lys Leu Glu
    210                 215                 220

Glu Glu Asn Ile Ala Thr Leu Phe Thr Met Cys Arg Asp Tyr Gly Arg
225                 230                 235                 240

Ser Ile Gly Phe Met Gly Asp Phe Tyr Ile Glu Pro Lys Pro Lys Glu
                245                 250                 255

Pro Met Lys His Gln Tyr Asp Phe Asp Ala Ala Thr Ala Ile Gly Phe
            260                 265                 270

Leu Arg Lys Tyr Gly Leu Asp Lys Asp Phe Lys Leu Asn Ile Glu Ala
```

```
                275                 280                 285
Asn His Ala Thr Leu Ala Gly His Thr Phe Gln His Glu Leu Arg Val
        290                 295                 300
Cys Ala Val Asn Gly Met Met Gly Ser Val Asp Ala Asn Gln Gly Asp
305                 310                 315                 320
Thr Leu Leu Gly Trp Asp Thr Asp Gln Phe Pro Thr Asn Val Tyr Asp
                325                 330                 335
Thr Thr Leu Ala Met Tyr Glu Ile Leu Lys Ala Gly Gly Leu Arg Gly
            340                 345                 350
Gly Leu Asn Phe Asp Ser Lys Asn Arg Arg Pro Ser Asn Thr Ala Asp
                355                 360                 365
Asp Met Phe Tyr Gly Phe Ile Ala Gly Met Asp Thr Phe Ala Leu Gly
        370                 375                 380
Leu Ile Lys Ala Ala Glu Ile Ile Glu Asp Gly Arg Ile Asp Asp Phe
385                 390                 395                 400
Val Lys Glu Arg Tyr Ala Ser Tyr Asn Ser Gly Ile Gly Lys Lys Ile
                405                 410                 415
Arg Asn Arg Lys Val Thr Leu Ile Glu Cys Ala Glu Tyr Ala Ala Lys
            420                 425                 430
Leu Lys Lys Pro Glu Leu Pro Glu Ser Gly Arg Gln Glu Tyr Leu Glu
                435                 440                 445
Ser Val Val Asn Asn Ile Leu Phe Gly
        450                 455

<210> SEQ ID NO 8
<211> LENGTH: 1371
<212> TYPE: DNA
<213> ORGANISM: artificial sequence
<220> FEATURE:
<223> OTHER INFORMATION: coding region for E. saburreum xylose isomerase
      optimized for expression in S. cerevisiae

<400> SEQUENCE: 8
atgaagacca agaacaacat catctgtact atcgctttga agggtgacat cttcatgaag    60
gagttcttcc caggtatctc tccagttaag ttcgagggta gagactctaa gaacccattg   120
tccttcaagt actacgacgc taagagagtt atcatgggta aaaccatgga agaacacttg   180
tctttcgcta tggcttggtg gcacaacttg tgtgcttgtg gtgttgacat gttcggtcaa   240
ggtactgtcg ataagtcctt cggtgaatct tccggtacta tggaacacgc tagagctaag   300
gttgacgctg gtatcgagtt catgaagaag ttgggtatca gtactactg tttccacgac   360
actgatatcg ttccagaaga ccaagaagat atcaacgtca ccaacgctag attggacgaa   420
atcactgatt acatcttgga aaagaccaag gacactgata tcaagtgttt gtggaccact   480
tgtaacatgt tctctaaccc aagattcatg aacggtgctg ttcttccaa ctccgctgac   540
gttttctgtt tcgctgctgc tcaagctaag aagggtttgg aaaacgctgt taagttgggt   600
gctaagggtt tcgtcttctg gggtggtaga gaaggttacg aaaccttgtt gaacactgac   660
atgaagttgg aagaagaaaa catcgctacc ttgttcacta tgtgtagaga ctacggtaga   720
tctatcggtt tcatgggtga cttctacatc gaaccaaagc caaggaacc aatgaagcac   780
caatacgact tcgatgctgc taccgctatc ggtttcttga aagtacgg tttggacaag   840
gatttcaagt tgaacatcga agctaaccac gctaccttgg ctggtcacac tttccaacac   900
gaattggaga tttgtgctgt caacggtatg atgggttctt tgacgctaa ccaaggtgac   960
actttgttgg gttgggacac cgatcaattc ccaactaacg tctacgacac cactttggct  1020
```

```
atgtacgaaa tcttgaaggc tggtggtttg agaggtggtt tgaacttcga ctctaagaac    1080
agaagaccat ccaacaccgc tgacgatatg ttctacggtt tcatcgctgg tatggacact    1140
ttcgctttgg gtttgatcaa ggctgctgaa atcatcgaag acggtagaat cgacgatttc    1200
gttaaggaaa gatacgcttc ttacaactcc ggtatcggta aaagatcag aaacagaaag    1260 gtcaccttga tcgaatgtgc tgaatacgct gctaagttga agaagccaga attgccagaa    1320
tccggtagac aagaatactt ggaatccgtc gtcaacaaca tcttgttcgg t             1371
```

<210> SEQ ID NO 9
<211> LENGTH: 441
<212> TYPE: PRT
<213> ORGANISM: Ruminococcus champanellensis

<400> SEQUENCE: 9

```
Met Ser Glu Phe Phe Thr Gly Ile Ser Lys Ile Pro Phe Glu Gly Lys
1               5                   10                  15

Ala Ser Asn Asn Pro Met Ala Phe Lys Tyr Tyr Asn Pro Asp Glu Val
            20                  25                  30

Val Gly Gly Lys Thr Met Arg Glu Gln Leu Lys Phe Ala Leu Ser Trp
        35                  40                  45

Trp His Thr Met Gly Gly Asp Gly Thr Asp Met Phe Gly Val Gly Thr
    50                  55                  60

Thr Asn Lys Lys Phe Gly Thr Asp Pro Met Asp Ile Ala Lys Arg
65                  70                  75                  80

Lys Val Asn Ala Ala Phe Glu Leu Met Asp Lys Leu Ser Ile Asp Tyr
                85                  90                  95

Phe Cys Phe His Asp Arg Asp Leu Ala Pro Glu Ala Asp Asn Leu Lys
            100                 105                 110

Glu Thr Asn Gln Arg Leu Asp Glu Ile Thr Glu Tyr Ile Ala Gln Met
        115                 120                 125

Met Gln Leu Asn Pro Asp Lys Lys Val Leu Trp Gly Thr Ala Asn Cys
    130                 135                 140

Phe Gly Asn Pro Arg Tyr Met His Gly Ala Gly Thr Ala Pro Asn Ala
145                 150                 155                 160

Asp Val Phe Ala Phe Ala Ala Gln Ile Lys Lys Ala Ile Glu Ile
                165                 170                 175

Thr Val Lys Leu Gly Gly Lys Gly Tyr Val Phe Trp Gly Gly Arg Glu
            180                 185                 190

Gly Tyr Glu Thr Leu Leu Asn Thr Asn Met Gly Leu Glu Leu Asp Asn
        195                 200                 205

Met Ala Arg Leu Leu His Met Ala Val Asp Tyr Ala Arg Ser Ile Gly
    210                 215                 220

Phe Thr Gly Asp Phe Tyr Ile Glu Pro Lys Pro Lys Glu Pro Thr Lys
225                 230                 235                 240

His Gln Tyr Asp Phe Asp Thr Ala Thr Val Ile Gly Phe Leu Arg Lys
                245                 250                 255

Tyr Asn Leu Asp Lys Asp Phe Lys Met Asn Ile Glu Ala Asn His Ala
            260                 265                 270

Thr Leu Ala Gln His Thr Phe His Glu Leu Arg Val Ala Arg Glu
        275                 280                 285

Asn Gly Phe Phe Gly Ser Ile Asp Ala Asn Gln Gly Asp Thr Leu Leu
    290                 295                 300

Gly Trp Asp Thr Asp Gln Phe Pro Thr Asn Thr Tyr Asp Ala Ala Leu
```

```
                305                 310                 315                 320
Cys Met Tyr Glu Val Leu Lys Ala Gly Gly Phe Thr Asn Gly Gly Leu
                    325                 330                 335

Asn Phe Asp Ser Lys Ala Arg Arg Gly Ser Phe Glu Met Glu Asp Ile
                    340                 345                 350

Phe His Ser Tyr Ile Ala Gly Met Asp Thr Phe Ala Leu Gly Leu Lys
                    355                 360                 365

Ile Ala Gln Lys Met Ile Asp Asp Gly Arg Ile Asp Gln Phe Val Ala
                    370                 375                 380

Asp Arg Tyr Ala Ser Trp Asn Thr Gly Ile Gly Ala Asp Ile Ile Ser
385                 390                 395                 400

Gly Lys Ala Thr Met Ala Asp Leu Glu Ala Tyr Ala Leu Ser Lys Gly
                    405                 410                 415

Asp Val Thr Ala Ser Leu Lys Ser Gly Arg Gln Glu Leu Leu Glu Ser
                    420                 425                 430

Ile Leu Asn Asn Ile Met Phe Asn Leu
                    435                 440

<210> SEQ ID NO 10
<211> LENGTH: 1323
<212> TYPE: DNA
<213> ORGANISM: artificial sequence
<220> FEATURE:
<223> OTHER INFORMATION: coding region for R. champanellensis xylose
      isomerase optimized for expression in S. cerevisiae

<400> SEQUENCE: 10
```

| | | | | | |
|---|---|---|---|---|---|
| atgtccgagt | tcttcactgg | tatctctaag | atcccattcg | aaggcaaggc | ttctaacaac | 60 |
| ccaatggctt | tcaagtacta | caacccagac | gaagttgtcg | gtggtaaaac | catgagagaa | 120 |
| caattgaagt | tcgctttgtc | ttggtggcac | accatggggtg | gtgacggtac | tgatatgttc | 180 |
| ggtgttggta | ctactaacaa | gaagttcggt | ggtactgacc | caatggatat | cgctaagaga | 240 |
| aaggtcaacg | ctgctttcga | attgatggac | aagttgtcca | tcgattactt | ctgtttccac | 300 |
| gacagagatt | tggctccaga | agctgacaac | ttgaaggaaa | ccaaccaaag | attggatgaa | 360 |
| atcactgaat | acatcgctca | aatgatgcaa | ttgaacccag | acaagaaggt | tttgtggggt | 420 |
| actgctaact | gtttcggtaa | cccaagatac | atgcacggtg | ctggtactgc | tccaaacgct | 480 |
| gacgttttcg | ctttcgctgc | tgctcaaatc | aagaaggcta | tcgaaatcac | cgttaagttg | 540 |
| ggtggtaaag | gttacgtctt | ctggggtggt | agagaaggtt | acgaaaccct | tgttgaacact | 600 |
| aacatgggtt | tggaattgga | caacatggct | agattgttgc | acatggctgt | tgactacgct | 660 |
| agatctatcg | gtttcaccgg | tgacttctac | atcgaaccaa | agccaaagga | accaactaag | 720 |
| caccaatacg | acttcgatac | cgctactgtc | atcggttttct | tgagaaagta | caacttggac | 780 |
| aaggatttca | agatgaacat | cgaagctaac | cacgctacct | ggctcaaca | cactttccaa | 840 |
| cacgaattga | gagttgctag | agaaaacggt | ttcttcggtt | ctatcgacgc | taaccaaggt | 900 |
| gacaccttgt | tgggttggga | cactgatcaa | ttcccaacca | acacttacga | cgctgctttg | 960 |
| tgtatgtacg | aagtcttgaa | ggctggtggt | ttcaccaacg | gtggtttgaa | cttcgactct | 1020 |
| aaggctagaa | gaggttcctt | cgaaatggaa | gacatcttcc | actcctacat | cgctggtatg | 1080 |
| gacactttcg | ctttgggttt | gaagatcgct | caaaagatga | tcgacgatgg | tagaatcgac | 1140 |
| caattcgttg | ctgatagata | cgcttcttgg | aacaccggta | tcggtgctga | catcatctcc | 1200 |
| ggtaaagcta | ccatggctga | cttggaagct | tacgctttgt | ctaagggtga | cgttactgct | 1260 |

```
tccttgaagt ccggtagaca agaattgttg gaatctatct tgaacaacat catgttcaac  1320
ttg                                                                1323
```

<210> SEQ ID NO 11
<211> LENGTH: 439
<212> TYPE: PRT
<213> ORGANISM: Ruminococcus flavefaciens

<400> SEQUENCE: 11

```
Met Glu Phe Phe Lys Asn Ile Ser Lys Ile Pro Tyr Glu Gly Lys Asp
1               5                   10                  15

Ser Thr Asn Pro Leu Ala Phe Lys Tyr Tyr Asn Pro Asp Glu Val Ile
            20                  25                  30

Asp Gly Lys Lys Met Arg Asp Ile Met Lys Phe Ala Leu Ser Trp Trp
        35                  40                  45

His Thr Met Gly Gly Asp Gly Thr Asp Met Phe Gly Cys Gly Thr Ala
    50                  55                  60

Asp Lys Thr Trp Gly Glu Asn Asp Pro Ala Ala Arg Ala Lys Ala Lys
65                  70                  75                  80

Val Asp Ala Ala Phe Glu Ile Met Gln Lys Leu Ser Ile Asp Tyr Phe
                85                  90                  95

Cys Phe His Asp Arg Asp Leu Ser Pro Glu Tyr Gly Ser Leu Lys Asp
            100                 105                 110

Thr Asn Ala Gln Leu Asp Ile Val Thr Asp Tyr Ile Lys Ala Lys Gln
        115                 120                 125

Ala Glu Thr Gly Leu Lys Cys Leu Trp Gly Thr Ala Lys Cys Phe Asp
    130                 135                 140

His Pro Arg Phe Met His Gly Ala Gly Thr Ser Pro Ser Ala Asp Val
145                 150                 155                 160

Phe Ala Phe Ser Ala Ala Gln Ile Lys Lys Ala Leu Glu Ser Thr Val
                165                 170                 175

Lys Leu Gly Gly Thr Gly Tyr Val Phe Trp Gly Gly Arg Glu Gly Tyr
            180                 185                 190

Glu Thr Leu Leu Asn Thr Asn Met Gly Leu Glu Leu Asp Asn Met Ala
        195                 200                 205

Arg Leu Met Lys Met Ala Val Glu Tyr Gly Arg Ser Ile Gly Phe Lys
    210                 215                 220

Gly Asp Phe Tyr Ile Glu Pro Lys Pro Lys Glu Pro Thr Lys His Gln
225                 230                 235                 240

Tyr Asp Phe Asp Thr Ala Thr Val Leu Gly Phe Leu Arg Lys Tyr Gly
                245                 250                 255

Leu Asp Lys Asp Phe Lys Met Asn Ile Glu Ala Asn His Ala Thr Leu
            260                 265                 270

Ala Gln His Thr Phe Gln His Glu Leu Cys Val Ala Arg Thr Asn Gly
        275                 280                 285

Ala Phe Gly Ser Ile Asp Ala Asn Gln Gly Asp Pro Leu Leu Gly Trp
    290                 295                 300

Asp Thr Asp Gln Phe Pro Thr Asn Ile Tyr Asp Thr Thr Met Cys Met
305                 310                 315                 320

Tyr Glu Val Ile Lys Ala Gly Gly Phe Thr Asn Gly Gly Leu Asn Phe
                325                 330                 335

Asp Ala Lys Ala Arg Arg Gly Ser Phe Thr Pro Glu Asp Ile Phe Tyr
            340                 345                 350

Ser Tyr Ile Ala Gly Met Asp Ala Phe Ala Leu Gly Tyr Lys Ala Ala
```

```
                355                 360                 365
Ser Lys Leu Ile Ala Asp Gly Arg Ile Asp Ser Phe Ile Ser Asp Arg
    370                 375                 380

Tyr Ala Ser Trp Ser Glu Gly Ile Gly Leu Asp Ile Ile Ser Gly Lys
385                 390                 395                 400

Ala Asp Met Ala Ala Leu Glu Lys Tyr Ala Leu Glu Lys Gly Glu Val
                405                 410                 415

Thr Asp Ser Ile Ser Ser Gly Arg Gln Glu Leu Leu Glu Ser Ile Val
            420                 425                 430

Asn Asn Val Ile Phe Asn Leu
        435

<210> SEQ ID NO 12
<211> LENGTH: 440
<212> TYPE: PRT
<213> ORGANISM: Abiotrophia defectiva

<400> SEQUENCE: 12

Met Ser Glu Leu Phe Gln Asn Ile Pro Lys Ile Lys Tyr Glu Gly Ala
1               5                   10                  15

Asn Ser Lys Asn Pro Leu Ala Phe His Tyr Tyr Asp Ala Glu Lys Ile
            20                  25                  30

Val Leu Gly Lys Thr Met Lys Glu His Leu Pro Phe Ala Met Ala Trp
        35                  40                  45

Trp His Asn Leu Cys Ala Ala Gly Thr Asp Met Phe Gly Arg Asp Thr
    50                  55                  60

Ala Asp Lys Ser Phe Gly Leu Glu Lys Gly Ser Met Glu His Ala Lys
65                  70                  75                  80

Ala Lys Val Asp Ala Gly Phe Glu Phe Met Glu Lys Leu Gly Ile Lys
                85                  90                  95

Tyr Phe Cys Phe His Asp Val Asp Leu Val Pro Glu Ala Cys Asp Ile
            100                 105                 110

Lys Glu Thr Asn Ser Arg Leu Asp Glu Ile Ser Asp Tyr Ile Leu Glu
        115                 120                 125

Lys Met Lys Gly Thr Asp Ile Lys Cys Leu Trp Gly Thr Ala Asn Met
    130                 135                 140

Phe Ser Asn Pro Arg Phe Val Asn Gly Ala Gly Ser Thr Asn Ser Ala
145                 150                 155                 160

Asp Val Tyr Cys Phe Ala Ala Ala Gln Ile Lys Lys Ala Leu Asp Ile
                165                 170                 175

Thr Val Lys Leu Gly Gly Arg Gly Tyr Val Phe Trp Gly Gly Arg Glu
            180                 185                 190

Gly Tyr Glu Thr Leu Leu Asn Thr Asp Val Lys Phe Glu Gln Glu Asn
        195                 200                 205

Ile Ala Asn Leu Met Lys Met Ala Val Glu Tyr Gly Arg Ser Ile Gly
    210                 215                 220

Phe Lys Gly Asp Phe Tyr Ile Glu Pro Lys Pro Lys Glu Pro Met Lys
225                 230                 235                 240

His Gln Tyr Asp Phe Asp Ala Ala Thr Ala Ile Gly Phe Leu Arg Gln
                245                 250                 255

Tyr Gly Leu Asp Lys Asp Phe Lys Leu Asn Ile Glu Ala Asn His Ala
            260                 265                 270

Thr Leu Ala Gly His Ser Phe Gln His Glu Leu Arg Ile Ser Ser Ile
        275                 280                 285
```

```
Asn Gly Met Leu Gly Ser Val Asp Ala Asn Gln Gly Asp Met Leu Leu
        290                 295                 300

Gly Trp Asp Thr Asp Glu Phe Pro Phe Asp Val Tyr Asp Thr Thr Met
305                 310                 315                 320

Cys Met Tyr Glu Val Leu Lys Asn Gly Gly Leu Thr Gly Gly Phe Asn
                325                 330                 335

Phe Asp Ala Lys Asn Arg Arg Pro Ser Tyr Thr Tyr Glu Asp Met Phe
                340                 345                 350

Tyr Gly Phe Ile Leu Gly Met Asp Ser Phe Ala Leu Gly Leu Ile Lys
            355                 360                 365

Ala Ala Lys Leu Ile Glu Glu Gly Thr Leu Asp Asn Phe Ile Lys Glu
        370                 375                 380

Arg Tyr Lys Ser Phe Glu Ser Glu Ile Gly Lys Lys Ile Arg Ser Lys
385                 390                 395                 400

Ser Ala Ser Leu Gln Glu Leu Ala Ala Tyr Ala Glu Met Gly Ala
                405                 410                 415

Pro Ala Met Pro Gly Ser Gly Arg Gln Glu Tyr Leu Gln Ala Ala Leu
                420                 425                 430

Asn Gln Asn Leu Phe Gly Glu Val
            435                 440

<210> SEQ ID NO 13
<211> LENGTH: 440
<212> TYPE: PRT
<213> ORGANISM: Leptotrichia goodfellowii

<400> SEQUENCE: 13

Met Lys Glu Phe Phe Pro Glu Ile Lys Glu Ile Lys Tyr Glu Gly Ala
1               5                   10                  15

Glu Ser Lys Asn Asp Leu Ala Phe Lys Tyr Tyr Asn Lys Asp Glu Val
                20                  25                  30

Leu Gly Gly Lys Thr Met Lys Glu His Leu Arg Phe Ala Met Ser Tyr
            35                  40                  45

Trp His Thr Leu Lys Ala Gln Gly Val Asp Met Phe Gly Gly Glu Thr
    50                  55                  60

Met Asp Arg Glu Trp Asn Lys Tyr Glu Asn Val Leu Glu Arg Ala Lys
65                  70                  75                  80

Ala Arg Ala Asn Ala Gly Phe Glu Phe Met Gln Lys Leu Gly Leu Glu
                85                  90                  95

Tyr Phe Cys Phe His Asp Arg Asp Ile Ile Asp Glu Ser Met Met Leu
                100                 105                 110

Ala Asp Ser Asn Lys Leu Leu Asp Glu Ile Val Asp His Ile Glu Glu
            115                 120                 125

Leu Met Lys Lys Thr Gly Arg Lys Leu Leu Trp Gly Thr Thr Asn Ala
        130                 135                 140

Phe Ser His Pro Arg Phe Val His Gly Ala Ser Thr Ser Pro Asn Ala
145                 150                 155                 160

Asp Val Phe Ala Tyr Ala Ala Ala Gln Val Lys Lys Ala Met Asp Ile
                165                 170                 175

Thr Asn Arg Leu Gly Gly Glu Asn Tyr Val Leu Trp Gly Gly Arg Glu
            180                 185                 190

Gly Tyr Glu Thr Leu Leu Asn Thr Asn Ser Glu Leu Glu Tyr Asp Asn
        195                 200                 205

Phe Ala Arg Phe Leu Lys Met Val Val Asp Tyr Lys Glu Lys Ile Gly
    210                 215                 220
```

```
Phe Lys Gly Gln Leu Leu Ile Glu Pro Lys Pro Lys Glu Pro Thr Lys
225                 230                 235                 240

His Gln Tyr Asp Phe Asp Thr Ala Thr Val Leu Ala Phe Leu Arg Lys
            245                 250                 255

Tyr Asn Leu Asp Lys Tyr Tyr Lys Val Asn Ile Glu Ala Asn His Ala
        260                 265                 270

Thr Leu Ala Gly His Thr Phe Gln His Glu Leu Asn Leu Ala Arg Ile
    275                 280                 285

Asn Gly Val Leu Gly Ser Ile Asp Ala Asn Gln Gly Asp Met Leu Leu
290                 295                 300

Gly Trp Asp Thr Asp Gln Phe Pro Thr Asn Ile Tyr Asp Thr Thr Leu
305                 310                 315                 320

Ala Met Tyr Glu Val Val Lys Asn Lys Gly Leu Gly Ser Gly Gly Leu
            325                 330                 335

Asn Phe Asp Ala Lys Val Arg Arg Gly Ser Phe Glu Asp Lys Asp Leu
        340                 345                 350

Phe Leu Ala Tyr Ile Ala Gly Met Asp Thr Phe Ala Lys Gly Leu Lys
    355                 360                 365

Ile Ala Tyr Arg Leu Tyr Glu Asp Lys Val Phe Glu Asp Phe Ile Asp
370                 375                 380

Lys Arg Tyr Glu Ser Tyr Lys Thr Gly Ile Gly Lys Asp Ile Ile Asp
385                 390                 395                 400

Gly Lys Val Gly Phe Glu Leu Ser Lys Tyr Ala Glu Thr Leu Thr
            405                 410                 415

Glu Val Lys Asn Asn Ser Gly Arg Gln Glu Met Leu Glu Ser Lys Leu
                420                 425                 430

Asn Gln Tyr Ile Phe Glu Val Lys
            435                 440

<210> SEQ ID NO 14
<211> LENGTH: 1320
<212> TYPE: DNA
<213> ORGANISM: artificial sequence
<220> FEATURE:
<223> OTHER INFORMATION: coding region for L. goodfellowii xylose
      isomerase optimized for expression in S. cerevisiae

<400> SEQUENCE: 14
atgaaggagt tcttcccaga aatcaaggaa atcaagtacg aaggtgctga atctaagaac    60
gatttggctt tcaagtacta caacaaggac gaagttttgg gtggtaaaac catgaaggaa   120
cacttgagat tcgctatgtc ttactggcac accttgaagg ctcaaggtgt tgacatgttc   180
ggtggtgaaa ctatggatag agaatggaac aagtacgaaa acgtcttgga aagagctaag   240
gctagagcta acgctggttt cgagttcatg caaaagttgg gtttggaata cttctgtttc   300
cacgacagag atatcatcga cgaatctatg atgttggctg attccaacaa gttgttggac   360
gaaatcgttg atcacatcga agaattgatg aagaagactg tagaaagtt gttgtggggt   420 actactaacg ctttctctca cccaagattc gtccacggtg cttctacctc cccaaacgct   480
gacgttttcg cttacgctgc tgctcaagtc aagaaggcta tggacatcac taacagattg   540
ggtggtgaaa actacgtttt gtggggtggt agagaaggtt acgaaacctt gttgaacact   600
aactccgaat ggaatacgca caacttcgct agattcttga gatggttgt cgattacaag   660 gaaaagatcg gttcaaggg tcaattgttg atcgaaccaa agccaaagga accaaccaag   720
caccaatacg acttcgatac cgctactgtt ttggcttct tgagaaagta caacttggac   780
```

-continued

```
aagtactaca aggtcaacat cgaagctaac cacgctacct tggctggtca cactttccaa    840
cacgaattga acttggctag aatcaacggt gtcttgggtt ctatcgacgc taaccaaggt    900
gacatgttgt tgggttggga caccgatcaa ttcccaacta acatctacga caccactttg    960
gctatgtacg aagttgtcaa gaacaagggt ttgggttctg gtggtttgaa cttcgacgct   1020
aaggttagaa gaggttcctt cgaagacaag gatttgttct tggcttacat cgctggtatg   1080
gacaccttcg ctaagggttt gaagatcgct tacagattgt acgaagacaa ggtcttcgaa   1140
gacttcatcg ataagagata cgaatcttac aagactggta tcggtaaaga catcatcgat   1200
ggtaaagttg gtttcgaaga attgtccaag tacgctgaaa ccttgactga agtcaagaac   1260
aactccggta gacaagaaat gttggaatct aagttgaacc aatacatctt cgaagtcaag   1320
```

<210> SEQ ID NO 15
<211> LENGTH: 440
<212> TYPE: PRT
<213> ORGANISM: Sebaldella termitidis

<400> SEQUENCE: 15

```
Met Lys Glu Tyr Phe Pro Glu Ile Lys Glu Ile Lys Tyr Glu Gly Pro
1               5                   10                  15

Glu Ser Lys Asn Val Met Ala Phe Lys Tyr Tyr Asn Lys Asp Glu Val
            20                  25                  30

Ile Gly Gly Lys Pro Met Arg Glu His Leu Lys Phe Ala Met Ser Tyr
        35                  40                  45

Trp His Thr Leu Lys Ala Gln Gly Leu Asp Met Phe Gly Gly Asp Thr
    50                  55                  60

Met Asp Arg Ala Trp Asn Arg Tyr Asp Asp Ala Leu Glu Gln Ala Lys
65                  70                  75                  80

Ala Arg Ala Asp Ala Gly Phe Glu Phe Met Gln Lys Ile Gly Met Asp
                85                  90                  95

Tyr Phe Cys Phe His Asp Arg Asp Ile Ile Asn Glu Ala Met Thr Leu
            100                 105                 110

Lys Glu Thr Asn Arg Leu Leu Asp Glu Ile Val Asp His Leu Glu Gly
        115                 120                 125

Leu Met Lys Lys Thr Gly Ile Lys Leu Leu Trp Gly Thr Thr Asn Ala
    130                 135                 140

Phe Ser His Pro Arg Phe Leu His Gly Gly Ala Thr Ala Pro Asn Ala
145                 150                 155                 160

Asp Val Phe Ala Tyr Ala Ala Ala Gln Val Lys Lys Ala Met Glu Ile
                165                 170                 175

Thr Lys Arg Leu Gly Gly Glu Asn Tyr Val Leu Trp Gly Gly Arg Glu
            180                 185                 190

Gly Tyr Glu Thr Leu Leu Asn Thr Lys Ser Asp Leu Glu Tyr Asp Asn
        195                 200                 205

Phe Ala Arg Phe Leu Gln Met Val Val Asp Tyr Lys Glu Lys Ile Gly
    210                 215                 220

Phe Glu Gly Gln Leu Leu Ile Glu Pro Lys Pro Lys Glu Pro Thr Lys
225                 230                 235                 240

His Gln Tyr Asp Phe Asp Thr Ala Thr Val Leu Gly Phe Leu Arg Lys
                245                 250                 255

Tyr Asn Leu Asp Lys His Tyr Lys Met Asn Ile Glu Ala Asn His Ala
            260                 265                 270

Thr Leu Ala Gly His Thr Phe Gln His Glu Leu Asn Leu Ala Arg Ile
```

```
                275                 280                 285
Asn Asn Val Met Gly Ser Ile Asp Ala Asn Gln Gly Asp Met Leu Leu
    290                 295                 300

Gly Trp Asp Thr Asp Gln Phe Pro Thr Asn Ile Tyr Asp Ala Val Leu
305                 310                 315                 320

Ala Met Tyr Glu Val Ile Lys Asn Asn Gly Leu Gly Lys Gly Gly Leu
                325                 330                 335

Asn Phe Asp Ala Lys Val Arg Arg Gly Ser Phe Glu Asp Lys Asp Leu
                340                 345                 350

Phe Leu Ala Tyr Ile Ala Gly Met Asp Thr Phe Ala Lys Gly Leu Thr
                355                 360                 365

Ile Ala Tyr Arg Leu Tyr Glu Asp Lys Val Phe Glu Asp Phe Gln Asp
    370                 375                 380

Lys Arg Tyr Glu Ser Tyr Lys Thr Gly Ile Gly Lys Asp Ile Val Glu
385                 390                 395                 400

Gly Lys Val Gly Phe Glu Glu Leu Ala Glu Tyr Val Glu Asn Leu Ala
                405                 410                 415

Glu Ile Lys Asn Thr Ser Gly Arg Gln Glu Met Leu Glu Ser Ile Leu
                420                 425                 430

Asn Ser Tyr Ile Leu Glu Ala Lys
                435                 440

<210> SEQ ID NO 16
<211> LENGTH: 1320
<212> TYPE: DNA
<213> ORGANISM: artificial sequence
<220> FEATURE:
<223> OTHER INFORMATION: coding region for S. termitidis xylose
      isomerase optimized for expression in S. cerevisiae

<400> SEQUENCE: 16
atgaaggaat acttcccaga aatcaaggaa atcaagtacg aaggtccaga atccaagaac      60
gttatggctt tcaagtacta caacaaggac gaagttatcg gtggtaaacc aatgagagaa     120
cacttgaagt cgctatatgt cttactggca cccttgaagg ctcaaggttt ggacatgttc     180
ggtggtgaca ctatggatag agcttggaac agatacgacg atgctttgga caagctaag      240 gctagagctg acgctggttt cgagttcatg caaaagatcg gtatggatta cttctgtttc     300
cacgacagag atatcatcaa cgaagctatg accttgaagg aaactaacag attgttggac     360
gaaatcgttg atcacttgga aggtttgatg aagaagaccg gtatcaagtt gttgtggggt     420
actactaacg ctttctctca cccaagattc ttgcacggtg gtgctaccgc tccaaacgct     480
gacgttttcg cttacgctgc tgctcaagtc aagaaggcta tggaaatcac taagagattg     540
ggtggtgaaa actacgtctt gtggggtggt agagaaggtt acgaaccctt gttgaacact     600
aagtccgact ggaatacgaa taacttcgct agattcttgc aaatggttgt tgactacaag     660
gaaaagatcg gtttcgaagg tcaattgttg atcgaaccaa agccaaagga accaactaag     720
caccaatacg acttcgatac cgctactgtt ttgggtttct tgagaaagta caacttggac     780
aagcactaca gatgaacat cgaagctaac cacgctacct ggctggtca cactttccaa     840 cacgaattga acttggctag aatcaacaac gtcatgggtt ctatcgacgc taaccaaggt     900
gacatgttgt tgggttggga caccgatcaa ttcccaacta acatctacga cgctgtttg      960 gctatgtacg aagtcatcaa gaacaacggt ttgggtaaag gtggttgaa cttcgacgct    1020 aaggtcagaa gaggttcctt cgaagacaag gatttgttct tggcttacat cgctggtatg   1080
```

-continued gacaccttcg ctaagggttt gactatcgct tacagattgt acgaagacaa ggttttcgaa 1140
gacttccaag ataagagata cgaatcttac aagaccggta tcggtaaaga catcgttgaa 1200
ggtaaagttg gtttcgaaga attggctgaa tacgtcgaaa acttggctga aatcaagaac 1260
acttccggta gacaagaaat gttggaatct atcttgaact cctacatctt ggaagctaag 1320

<210> SEQ ID NO 17
<211> LENGTH: 9910
<212> TYPE: DNA
<213> ORGANISM: artificial sequence
<220> FEATURE:
<223> OTHER INFORMATION: constructed vector for Hm1 expression

<400> SEQUENCE: 17
aggccagagg aaaataatat caagtgctgg aaactttttc tcttggaatt tttgcaacat 60
caagtcatag tcaattgaat tgacccaatt tcacatttaa gattttttttt ttttcatccg 120 acatacatct gtacactagg aagccctgtt tttctgaagc agcttcaaat atatatattt 180
tttacatatt tattatgatt caatgaacaa tctaattaaa tcgaaaacaa gaaccgaaac 240
gcgaataaat aatttattta gatggtgaca agtgtataag tcctcatcgg gacagctacg 300
atttctcttt cggttttggc tgagctactg gttgctgtga cgcagcggca ttagcgcggc 360
gttatgagct accctcgtgg cctgaaagat ggcgggaata aagcggaact aaaaattact 420
gactgagcca tattgaggtc aatttgtcaa ctcgtcaagt cacgtttggt ggacggcccc 480
tttccaacga atcgtatata ctaacatgcg cgcgcttcct atatacacat atacatatat 540
atatatatat atatgtgtgc gtgtatgtgt acacctgtat ttaatttcct tactcgcggg 600
tttttctttt ttctcaattc ttggcttcct ctttctcgag cggaccggat cctccgcggt 660
gccggcagat ctatttaaat ggcgcgccga cgtcaggtgg cacttttcgg ggaaatgtgc 720
gcggaacccc tatttgttta tttttctaaa tacattcaaa tatgtatccg ctcatgagac 780
aataaccctg ataaatgctt caataatatt gaaaaaggaa gagtatgagt attcaacatt 840
tccgtgtcgc ccttattccc ttttttgcgg cattttgcct tcctgttttt gctcacccag 900
aaacgctggt gaaagtaaaa gatgctgaag atcagttggg tgcacgagtg ggttacatcg 960
aactggatct caacagcggt aagatccttg agagttttcg ccccgaagaa cgttttccaa 1020
tgatgagcac ttttaaagtt ctgctatgtg gcgcggtatt atcccgtatt gacgccgggc 1080
aagagcaact cggtcgccgc atacactatt ctcagaatga cttggttgag tactcaccag 1140
tcacagaaaa gcatcttacg gatggcatga cagtaagaga attatgcagt gctgccataa 1200
ccatgagtga taacactgcg gccaacttac ttctgacaac gatcggagga ccgaaggagc 1260
taaccgcttt tttgcacaac atgggggatc atgtaactcg ccttgatcgt tgggaaccgg 1320
agctgaatga agccatacca aacgacgagc gtgacaccac gatgcctgta gcaatggcaa 1380
caacgttgcg caaactatta actggcgaac tacttactct agcttcccgg caacaattaa 1440
tagactggat ggaggcggat aaagttgcag gaccacttct gcgctcggcc cttccggctg 1500
gctggtttat tgctgataaa tctggagccg gtgagcgtgg gtctcgcggt atcattgcag 1560
cactggggcc agatggtaag ccctcccgta tcgtagttat ctacacgacg gggagtcagg 1620
caactatgga tgaacgaaat agacagatcg ctgagatagg tgcctcactg attaagcatt 1680
ggtaactgtc agaccaagtt tactcatata tactttagat tgatttaaaa cttcattttt 1740
aatttaaaag gatctaggtg aagatccttt ttgataatct catgaccaaa atcccttaac 1800
gtgagttttc gttccactga gcgtcagacc ccgtagaaaa gatcaaagga tcttcttgag 1860

```
atccttttttt tctgcgcgta atctgctgct tgcaaacaaa aaaaccaccg ctaccagcgg    1920
tggtttgttt gccggatcaa gagctaccaa ctcttttttcc gaaggtaact ggcttcagca    1980
gagcgcagat accaaatact gttcttctag tgtagccgta gttaggccac cacttcaaga    2040
actctgtagc accgcctaca tacctcgctc tgctaatcct gttaccagtg gctgctgcca    2100
gtggcgataa gtcgtgtctt accgggttgg actcaagacg atagttaccg gataaggcgc    2160
agcggtcggg ctgaacgggg ggttcgtgca cacagcccag cttggagcga acgacctaca    2220
ccgaactgag atacctacag cgtgagctat gagaaagcgc cacgcttccc gaagggagaa    2280
aggcggacag gtatccggta agcggcaggg tcggaacagg agagcgcacg agggagcttc    2340 caggggggaaa cgcctggtat ctttatagtc ctgtcgggtt tcgccacctc tgacttgagc    2400
gtcgattttt gtgatgctcg tcaggggggc ggagcctatg gaaaaacgcc agcaacgcgg    2460 ccttttttacg gttcctggcc ttttgctggc cttttgctca catgttcttt cctgcgttat    2520
cccctgattc tgtggataac cgtattaccg ccttttgagtg agctgatacc gctcgccgca    2580
gccgaacgac cgagcgcagc gagtcagtga gcgaggaagc ggaagagcgc ccaatacgca    2640
aaccgcctct ccccgcgcgt tggccgattc attaatgcag ctggcacgac aggtttcccg    2700
actggaaagc gggcagtgag cgcaacgcaa ttaatgtgag ttagctcact cattaggcac    2760
cccaggcttt acactttatg cttccggctc gtatgttgtg tggaattgtg agcggataac    2820
aatttcacac aggaaacagc tatgaccatg attacgccaa gcttttttctt ccaattttt    2880 ttttttttcgt cattataaaa atcattacga ccgagattcc cgggtaataa ctgatataat    2940
taaattgaag ctctaatttg tgagttttagt atacatgcat ttacttataa tacagttttt    3000
tagttttgct ggccgcatct tctcaaatat gcttcccagc ctgcttttct gtaacgttca    3060
ccctctacct tagcatccct tccctttgca aatagtcctc ttccaacaat aataatgtca    3120
gatcctgtag agaccacatc atccacggtt ctatactgtt gacccaatgc gtctcccttg    3180
tcatctaaac ccacaccggg tgtcataatc aaccaatcgt aaccttcatc tcttccaccc    3240
atgtctcttt gagcaataaa gccgataaca aaatctttgt cgctcttcgc aatgtcaaca    3300 gtaccccttag tatattctcc agtagatagg gagcccttgc atgacaattc tgctaacatc    3360
aaaaggcctc taggttcctt tgttacttct tctgccgcct gcttcaaacc gctaacaata    3420
cctgggccca ccacaccgtg tgcattcgta atgtctgccc attctgctat tctgtataca    3480
cccgcagagt actgcaattt gactgtatta ccaatgtcag caaattttct gtcttcgaag    3540
agtaaaaaat tgtacttggc ggataatgcc tttagcggct taactgtgcc ctccatggaa    3600
aaatcagtca agatatccac atgtgttttt agtaaacaaa ttttgggacc taatgcttca    3660
actaactcca gtaattcctt ggtggtacga acatccaatg aagcacacaa gtttgtttgc    3720
ttttcgtgca tgatattaaa tagcttggca gcaacaggac taggatgagt agcagcacgt    3780
tccttatatg tagctttcga catgatttat cttcgtttcc tgcaggtttt tgttctgtgc    3840
agttgggtta agaatactgg gcaatttcat gtttcttcaa cactacatat gcgtatatat    3900
accaatctaa gtctgtgctc cttccttcgt tcttccttct gttcggagat taccgaatca    3960
aaaaaatttc aaggaaaccg aaatcaaaaa aagaataaaa aaaaaatga tgaattgaaa    4020 agcttgcatg cctgcaggtc gactctagta tactccgtct actgtacgat acacttccgc    4080
tcaggtcctt gtccttttaac gaggcttac cactctttttg ttactctatt gatccagctc    4140
agcaaaggca gtgtgatcta agattctatc ttcgcgatgt agtaaaacta gctagaccga    4200
```

-continued

```
gaaagagact agaaatgcaa aaggcacttc tacaatggct gccatcatta ttatccgatg    4260
tgacgctgca tttttttttt tttttttttt tttttttttt tttttttttt tttttttttt    4320
ttgtacaaat atcataaaaa aagagaatct ttttaagcaa ggattttctt aacttcttcg    4380
gcgacagcat caccgacttc ggtggtactg ttggaaccac ctaaatcacc agttctgata    4440
cctgcatcca aaaccttttt aactgcatct tcaatggctt taccttcttc aggcaagttc    4500
aatgacaatt tcaacatcat tgcagcagac aagatagtgg cgatagggtt gaccttattc    4560
tttggcaaat ctggagcgga accatggcat ggttcgtaca aaccaaatgc ggtgttcttg    4620
tctggcaaag aggccaagga cgcagatggc aacaaaccca aggagcctgg ataacggag     4680
gcttcatcgg agatgatatc accaaacatg ttgctggtga ttataatacc atttaggtgg    4740
gttgggttct taactaggat catggcggca gaatcaatca attgatgttg aactttcaat    4800
gtagggaatt cgttcttgat ggtttcctcc acagtttttc tccataatct tgaagaggcc    4860
aaaacattag ctttatccaa ggaccaaata ggcaatggtg gctcatgttg tagggccatg    4920
aaagcggcca ttcttgtgat tctttgcact tctggaacgg tgtattgttc actatcccaa    4980
gcgacaccat caccatcgtc ttcctttctc ttaccaaagt aaatacctcc cactaattct    5040
ctaacaacaa cgaagtcagt accttttagca aattgtggct tgattggaga taagtctaaa   5100
agagagtcgg atgcaaagtt acatggtctt aagttggcgt acaattgaag ttctttacgg    5160
atttttagta aaccttgttc aggtctaaca ctaccggtac cccatttagg accacccaca    5220
gcacctaaca aaacggcatc agccttcttg gaggcttcca gcgcctcatc tggaagtgga    5280
acacctgtag catcgatagc agcaccacca attaaatgat tttcgaaatc gaacttgaca    5340
ttggaacgaa catcagaaat agctttaaga accttaatgg cttcggctgt gatttcttga    5400
ccaacgtggt cacctggcaa aacgacgatc ttccttaggg gcagacattac aatggtatat   5460
ccttgaaata tatataaaaa aaaaaaaaaa aaaaaaaaaa aaaaatgcag cttctcaatg    5520
atattcgaat acgctttgag gagatacagc ctaatatccg acaaactgtt ttacagattt    5580
acgatcgtac ttgttaccca tcattgaatt ttgaacatcc gaacctggga gttttccctg    5640
aaacagatag tatatttgaa cctgtataat aatatatagt ctagcgcttt acggaagaca    5700
atgtatgtat ttcggttcct ggagaaacta ttgcatctat tgcataggta atcttgcacg    5760
tcgcatcccc ggttcatttt ctgcgtttcc atcttgcact tcaatagcat atctttgtta    5820
acgaagcatc tgtgcttcat tttgtagaac aaaaatgcaa cgcgagagcg ctaatttttc    5880
aaacaaagaa tctgagctgc attttttacag aacagaaatg caacgcgaaa gcgctatttt   5940
accaacgaag aatctgtgct tcattttgt aaaacaaaaa tgcaacgcga gagcgctaat    6000
ttttcaaaca aagaatctga gctgcatttt tacagaacag aaatgcaacg cgagagcgct    6060
attttaccaa caaagaatct atacttcttt tttgttctac aaaaatgcat cccgagagcg    6120
ctattttttct aacaaagcat cttagattac tttttttctc ctttgtgcgc tctataatgc   6180
agtctcttga taacttttg cactgtaggt ccgttaaggt tagaagaagg ctactttggt     6240
gtctatttc tcttccataa aaaaagcctg actccacttc ccgcgtttac tgattactag     6300
cgaagctgcg ggtgcatttt ttcaagataa aggcatcccc gattatattc tataccgatg    6360
tggattgcgc atactttgtg aacagaaagt gatagcgttg atgattcttc attggtcaga    6420
aaattatgaa cggtttcttc tattttgtct ctatatacta cgtataggaa atgtttacat    6480
tttcgtattg ttttcgattc actctatgaa tagttcttac tacaattttt ttgtctaaag    6540
agtaatacta gagataaaca taaaaaatgt agaggtcgag tttagatgca agttcaagga    6600
```

-continued

```
gcgaaaggtg gatgggtagg ttatataggg atatagcaca gagatatata gcaaagagat    6660
acttttgagc aatgtttgtg gaagcggtat tcgcaatatt ttagtagctc gttacagtcc    6720
ggtgcgtttt tggttttttg aaagtgcgtc ttcagagcgc ttttggtttt caaaagcgct    6780
ctgaagttcc tatactttct agagaatagg aacttcggaa taggaacttc aaagcgtttc    6840
cgaaaacgag cgcttccgaa aatgcaacgc gagctgcgca catacagctc actgttcacg    6900
tcgcacctat atctgcgtgt tgcctgtata tatatataca tgagaagaac ggcatagtgc    6960
gtgtttatgc ttaaatgcgt acttatatgc gtctatttat gtaggatgaa aggtagtcta    7020
gtacctcctg tgatattatc ccattccatg cggggtatcg tatgcttcct tcagcactac    7080
cctttagctg ttctatatgc tgccactcct caattggatt agtctcatcc ttcaatgcta    7140
tcatttcctt tgatattgga tcatatgcat agtaccgaga aactagagga tctcccatta    7200
ccgacatttg ggcgctatac gtgcatatgt tcatgtatgt atctgtattt aaaacacttt    7260
tgtattattt ttcctcatat atgtgtatag gtttatacgg atgatttaat tattacttca    7320
ccacccttta tttcaggctg atatcttagc cttgttacta gtcaccggtg gcggccgcac    7380
ctggtaaaac ctctagtgga gtagtagatg taatcaatga agcggaagcc aaaagaccag    7440
agtagaggcc tatagaagaa actgcgatac cttttgtgat ggctaaacaa acagacatct    7500
ttttatatgt ttttacttct gtatatcgtg aagtagtaag tgataagcga atttggctaa    7560
gaacgttgta agtgaacaag ggacctcttt tgcctttcaa aaaaggatta aatggagtta    7620
atcattgaga tttagttttc gttagattct gtatccctaa ataactccct tacccgacgg    7680
gaaggcacaa aagacttgaa taatagcaaa cggccagtag ccaagaccaa ataatactag    7740
agttaactga tggtcttaaa caggcattac gtggtgaact ccaagaccaa tatacaaaat    7800
atcgataagt tattcttgcc caccaattta aggagcctac atcaggacag tagtaccatt    7860
cctcagagaa gaggtataca taacaagaaa atcgcgtgaa caccttatat aacttagccc    7920
gttattgagc taaaaaacct tgcaaaattt cctatgaata agaatacttc agacgtgata    7980
aaaatttact ttctaactct tctcacgctg cccctatctg ttcttccgct ctaccgtgag    8040
aaataaagca tcgagtacgg cagttcgctg tcactgaact aaaacaataa ggctagttcg    8100
aatgatgaac ttgcttgctg tcaaacttct gagttgccgc tgatgtgaca ctgtgacaat    8160
aaattcaaac cggttatagc ggtctcctcc ggtaccggtt ctgccacctc caatagagct    8220
cagtaggagt cagaacctct gcggtggctg tcagtgactc atccgcgttt cgtaagttgt    8280
gcgcgtgcac atttcgcccg ttcccgctca tcttgcagca ggcggaaatt ttcatcacgc    8340
tgtaggacgc aaaaaaaaaa taattaatcg tacaagaatc ttggaaaaaa aattgaaaaa    8400
ttttgtataa aagggatgac ctaacttgac tcaatggctt ttacacccag tattttccct    8460
ttccttgttt gttacaatta tagaagcaag acaaaaacat atagacaacc tattcctagg    8520
agttatattt ttttaccccta ccagcaatat aagtaaaaaa ctgtttaaac agtatgaagg    8580
agttcttccc atccatctct ccaatcaagt tcgaaggttc cgaatccaag aacccattgt    8640
ctttcaagta ctacgacgct aagagagtta tcatgggtaa aaccatggaa gaacacttgt    8700
ctttcgctat ggcttggtgg cacaacttgt gtgcttccgg tgttgacatg ttcggtcaag    8760
gtactgctga caagggtttc ggtgaaaact tgggtactat ggaacacgct aaggctaagg    8820
ttgacgctgg tatcgagttc atgcaaaagt tgggtatcaa gtactactgt ttccacgaca    8880
ccgatatcgt tccagaagac caagaagata tcaacgtcac caacgctaga ttggacgaaa    8940
```

```
tcactgatta catcttggaa aagaccaagg gtactgacat caagtgtttg tgggctactt    9000
gtaacatgtt ctctaaccca agattcatga acggtgctgg ttcttctaac tctgctgacg    9060
ttttctgttt cgctgctgct caagctaaga agggtttgga aaacgctgtt aagttgggtg    9120
ctaagggttt cgtcttctgg ggtggtagag aaggttacga aaccttgttg aacactgaca    9180
tgaagttgga agaagaaaac atcgctacct tgttcactat gtgtagagac tacggtagat    9240
ctatcggttt caagggtgac ttctacatcg aaccaaagcc aaaggaacca atgaagcacc    9300
aatacgactt cgatgctgct accgctatcg gtttcttgag aaagtacggt ttggacaagg    9360
atttcaagat gaacatcgaa gctaaccacg ctaccttggc tggtcacact ttccaacacg    9420
aattgagagt ttctgctatc aacggtatgt tgggttccgt tgacgctaac caaggtgaca    9480
ctttgttggg ttgggacacc gatcaattcc caactaacgt ttacgacacc actttggcta    9540
tgtacgaaat cttgaaggct ggtggtttgt ctggtggttt gaacttcgac tctaagaaca    9600
gaagaccatc caacaccgct gaagacatgt ctctacggttt catcgctggt atggacactt    9660
tcgctttggg tttgatcaag gctgctcaaa tcatcgaaga cggtagaatc gatgaatttg    9720
tcaaggaaag atactcttcc tacaactctg gtatcggtga aaagatcaga aacagatccg    9780
ttactttggt cgaatgtgct gaatacgctt tgaagatgaa gaagccagaa ttgccagaat    9840
ctggtagaca agaatacttg gaaaccgtcg tcaacaacat cttcttcaac tctaagttgt    9900
gaggccctgc                                                           9910

<210> SEQ ID NO 18
<211> LENGTH: 16404
<212> TYPE: DNA
<213> ORGANISM: Artificial sequence
<220> FEATURE:
<223> OTHER INFORMATION: constructed plasmid

<400> SEQUENCE: 18
gatccacgat cgcattgcgg attacgtatt ctaatgttca gtaccgttcg tataatgtat      60
gctatacgaa gttatgcaga ttgtactgag agtgcaccat accacagctt tcaattcaa     120
ttcatcattt ttttttttatt cttttttttg atttcggttt ctttgaaatt ttttttgattc    180
ggtaatctcc gaacagaagg aagaacgaag gaaggagcac agacttagat tggtatatat    240
acgcatatgt agtgttgaag aaacatgaaa ttgcccagta ttcttaaccc aactgcacag    300
aacaaaaacc tgcaggaaac gaagataaat catgtcgaaa gctacatata aggaacgtgc    360
tgctactcat cctagtcctg ttgctgccaa gctatttaat atcatgcacg aaaagcaaac    420
aaacttgtgt gcttcattgg atgttcgtac caccaaggaa ttactggagt tagttgaagc    480
attaggtccc aaaatttgtt tactaaaaac acatgtggat atcttgactg attttttccat    540
ggagggcaca gttaagccgc taaaggcatt atccgccaag tacaattttt tactcttcga    600
agacagaaaa tttgctgaca ttggtaatac agtcaaattg cagtactctg cgggtgtata    660
cagaatagca gaatgggcag acattacgaa tgcacacggt gtggtgggcc caggtattgt    720
tagcggtttg aagcaggcgg cagaagaagt aacaaaggaa cctagaggcc ttttgatgtt    780
agcagaattg tcatgcaagg gctccctatc tactggagaa tatactaagg gtactgttga    840
cattgcgaag agcgacaaag attttgttat cggctttatt gctcaaagag acatgggtgg    900
aagagatgaa ggttacgatt ggttgattat gacacccggt gtgggtttag atgacaaggg    960
agacgcattg ggtcaacagt atagaaccgt ggatgatgtg gtctctacag gatctgacat   1020
tattattgtt ggaagaggac tatttgcaaa gggaagggat gctaaggtag agggtgaacg   1080
```

-continued

```
ttacagaaaa gcaggctggg aagcatattt gagaagatgc ggccagcaaa actaaaaaac    1140
tgtattataa gtaaatgcat gtatactaaa ctcacaaatt agagcttcaa tttaattata    1200
tcagttatta ccctatgcgg tgtgaaatac cgcacagatg cgtaaggaga aaataccgca    1260
tcaggaaatt gtaaacgtta atattttgtt aaaattcgcg ttaaatttttt gttaaatcag    1320
ctcattttttt aaccaatagg ccgaaatcgg caaaatccct tataaatcaa agaatagac    1380
cgagataggg ttgagtgttg ttccagtttg aacaagagt ccactattaa agaacgtgga    1440
ctccaacgtc aaagggcgaa aaaccgtcta tcagggcgat ggcccactac gtgaaccatc    1500
accctaatca agataacttc gtataatgta tgctatacga acggtacccg ccaactctgt    1560
tcgagaatga tgtaatcaag aaggtctcac aaaaccatcc aggcagtacc acttcccaag    1620
tattgcttag atgggcaact cagagaggca ttgccgtcat tccaaaatct tccaagaagg    1680
aaaggttact tggcaaccta gaaatcgaaa aaagttcac tttaacggag caagaattga    1740
aggatatttc tgcactaaat gccaacatca gatttaatga tccatggacc tggttggatg    1800
gtaaattccc cacttttgcc tgatccagcc agtaaaatcc atactcaacg acgatatgaa    1860
caaatttccc tcattccgat gctgtatatg tgtataaatt tttacatgct cttctgttta    1920
gacacagaac agctttaaat aaaatgttgg atatacttttt tctgcctgtg gtgtcatcca    1980
cgcttttaat tcatctcttg tatggttgac aatttggcta ttttttaaca gaacccaacg    2040
gtaattgaaa ttaaagggga aacgagtggg ggcgatgagt gagtgatacg gcgcctgatg    2100
cggtattttc tccttacgca tctgtgcggt atttcacacc gcatatggtg cactctcagt    2160
acaatctgct ctgatgccgc atagttaagc cagccccgac acccgccaac acccgctgac    2220
gcgccctgac gggcttgtct gctcccggca tccgcttaca gacaagctgt gaccgtctcc    2280
gggagctgca tgtgtcagag gttttcaccg tcatcaccga aacgcgcgag acgaaagggc    2340
ctcgtgatac gcctattttt ataggttaat gtcatgataa taatggtttc ttagacgtca    2400
ggtggcactt ttcggggaaa tgtgcgcgga acccctattt gtttatttttt ctaaatacat    2460
tcaaatatgt atccgctcat gagacaataa ccctgataaa tgcttcaata atattgaaaa    2520
aggaagagta tgagtattca acatttccgt gtcgccctta ttccctttttt tgcggcattt    2580
tgccttcctg tttttgctca cccagaaacg ctggtgaaag taaaagatgc tgaagatcag    2640
ttgggtgcac gagtgggtta catcgaactg gatctcaaca gcggtaagat ccttgagagt    2700
tttcgccccg aagaacgttt tccaatgatg agcactttta aagttctgct atgtggcgcg    2760
gtattatccc gtattgacgc cgggcaagag caactcggtc gccgcataca ctattctcag    2820
aatgacttgg ttgagtactc accagtcaca gaaaagcatc ttacggatgg catgacagta    2880
agagaattat gcagtgctgc cataaccatg agtgataaca ctgcggccaa cttacttctg    2940
acaacgatcg gaggaccgaa ggagctaacc gcttttttgc acaacatggg ggatcatgta    3000
actcgccttg atcgttggga accggagctg aatgaagcca taccaaacga cgagcgtgac    3060
accacgatgc ctgtagcaat ggcaacaacg ttgcgcaaac tattaactgg cgaactactt    3120
actctagctt cccggcaaca attaatagac tggatggagg cggataaagt tgcaggacca    3180
cttctgcgct cggcccttcc ggctggctgg tttattgctg ataaatctgg agccggtgag    3240
cgtgggtctc gcggtatcat tgcagcactg gggccagatg gtaagccctc ccgtatcgta    3300
gttatctaca cgacggggag tcaggcaact atggatgaac gaaatagaca gatcgctgag    3360
ataggtgcct cactgattaa gcattggtaa ctgtcagacc aagtttactc atatatactt    3420
```

```
tagattgatt taaaacttca tttttaattt aaaaggatct aggtgaagat ccttttgat    3480
aatctcatga ccaaaatccc ttaacgtgag ttttcgttcc actgagcgtc agacccgta    3540
gaaaagatca aaggatcttc ttgagatcct ttttttctgc gcgtaatctg ctgcttgcaa   3600
acaaaaaaac caccgctacc agcggtggtt tgtttgccgg atcaagagct accaactctt   3660
tttccgaagg taactggctt cagcagagcg cagataccaa atactgtcct tctagtgtag   3720
ccgtagttag gccaccactt caagaactct gtagcaccgc ctacatacct cgctctgcta   3780
atcctgttac cagtggctgc tgccagtggc gataagtcgt gtcttaccgg gttggactca   3840
agacgatagt taccggataa ggcgcagcgg tcgggctgaa cggggggttc gtgcacacag   3900
cccagcttgg agcgaacgac ctacaccgaa ctgagatacc tacagcgtga gctatgagaa   3960
agcgccacgc ttcccgaagg gagaaaggcg gacaggtatc cggtaagcgg cagggtcgga   4020
acaggagagc gcacgaggga gcttccaggg ggaaacgcct ggtatcttta tagtcctgtc   4080
gggtttcgcc acctctgact tgagcgtcga ttttttgtgat gctcgtcagg ggggcggagc   4140
ctatggaaaa acgccagcaa cgcggccttt ttacggttcc tggccttttg ctggcctttt   4200
gctcacatgt tctttcctgc gttatcccct gattctgtgg ataaccgtat taccgccttt   4260
gagtgagctg ataccgctcg ccgcagccga acgaccgagc gcagcgagtc agtgagcgag   4320
gaagcggaag agcgcccaat acgcaaaccg cctctccccg cgcgttggcc gattcattaa   4380
tgcagctggc acgacaggtt tcccgactgg aaagcgggca gtgagcgcaa cgcaattaat   4440
gtgagttagc tcactcatta ggcaccccag gctttacact ttatgcttcc ggctcgtatg   4500
ttgtgtggaa ttgtgagcgg ataacaattt cacacaggaa acagctatga ccatgattag   4560
gcgcctactt ctaggggcc tatcaagtaa attactcctg gtacactgaa gtatataagg    4620
gatatagaag caaatagttg tcagtgcaat ccttcaagac gattgggaaa atactgtaat   4680
ataaatcgta aggaaaatt ggaaattttt taaagatgtc ttcactggtt actcttaata    4740
acggtctgaa aatgccccta gtcggcttag ggtgctggaa aattgacaaa aaagtctgtg   4800
cgaatcaaat ttatgaagct atcaaattag gctaccgttt attcgatggt gcttgcgact   4860
acggcaacga aaaggaagtt ggtgaaggta tcaggaaagc catctccgaa ggtcttgttt   4920
ctagaaagga tatatttgtt gtttcaaagt tatggaacaa ttttcaccat cctgatcatg   4980
taaaattagc tttaaagaag accttaagcg atatgggact tgattattta gacctgtatt   5040
atattcactt cccaatcgcc ttcaaatatg ttccatttga agagaaatac cctccaggat   5100
tctatacggg cgcagaagga ttctatacgg gcgcagaact agtgatctcg aggttccaga   5160
gctcggatcc accacaggtg ttgtcctctg aggacataaa atacacaccg agattcatca   5220
actcattgct ggagttagca tatctacaat tgggtgaaat ggggagcgat ttgcaggcat   5280
ttgctcggca tgccggtaga ggtgtggtca ataagagcga cctcatgcta tacctgagaa   5340
agcaacctga cctacaggaa agagttactc aagaataaga attttcgttt taaaacctaa   5400
gagtcacttt aaaatttgta tacacttatt ttttttataa cttatttaat aataaaaatc   5460
ataaatcata agaaattcgc ttactcatcc cgggttagat gagagtcttt tccagttcgc   5520
ttaagggac aatcttggaa ttatagcgat cccaattttc attatccaca tcggatatgc   5580
tttccattac atgccatgga aaattgtcat tcagaaattt atcaaaagga actgcaattt   5640
tattagagtc atataacaat gaccacatgg cctataaca accaccaagg gcacatgagt   5700
ttggtgtttc tagcctaaaa ttaccctttg tagcaccaat gacttgagca aacttcttca   5760
caatagcatc gttttttagaa gccccaccta caaaaaagt cctttctggc cttttattta   5820
```

```
ggtagtcccg cagcggagat tcatcgtaat caaacttcac gattgtatct tcgttcagtc   5880
tctgttgtga gcttgcgttt gaatccgaaa gcaggggaga tattcttacc ctgcaactta   5940
aagcctgtga ttctacaata ttttggcat cgtgcctctt gtctttgaac ttggccacct    6000
ctctttcaat catacccgtt tttggattga agataaccct tttgtttatg gcttttacgc   6060
taggaacgat ctcccccaga ggaaaatata cacctaattc attttcacta ctttctgagt   6120
catctagcac agcttgatta aaagagtcc aatcgttagt cttctcataa ttattttccc    6180
gttctttgtt taactcgtct cttatcctct cccttgccaa agaaccatta caataacaaa   6240
tcatacccat ataatggttt ggcagagttg atgaatgaa agatgatag ttcggagagg     6300 ggtgatactt atcggtgacc agaagaactg tagtacttgt tcctagggaa acgagaacgt   6360
cattcttccg caggggtaaa gaacatatag tggctaaatt atccccagtc atgggagaga   6420
ccttgcagtt tgtattgaaa ccgtacttct caataaaata tttacagatg gtacccgcta   6480
tcaaattttt catgggtgct ctcattaatt tttgtctgat agttttatcc ttagaagaac   6540
tatcaattag atgtagtagc tcatcactga attttctttc acgtatatca taaaggttca   6600
taccacaggc atctgcctcc tctaattcaa caagatggcc cactaagata gaagtcaaaa   6660
aattagacac taaagaaatg gtctttgttt tttcgtaagc ttctggttct aattgtgcaa   6720
ttttcagaat ttgaggacca gtaaatctaa aatgggctct ggaccctgtt aattgagcca   6780
ttttttcagg cccacctatg cactcttcaa actcttgaca ttgctttgca gtactgtggt   6840
cttgccaatt gggggcggtt tgccttgcaa atgctacaga gctcacgtag tgcaataaat   6900 cttttttccgg tttcttattc aattgctcta acagagattc ggcttgggag gaccagtaga   6960 cagaccgtg ctgctggcag gaccctgaga cggccataac tttgttcaat ggaaatttag    7020
cctcgcgata tttcgagaga accagatcta gagcctctaa ccacatggct acgggacatt   7080
cgatagtgtc gccgtgtata tagacaccct tctttgtgtg ataatgcgga agatcctttt   7140
caaattccac tgtttctgaa tggacaattt ttaggtcctg gttaatggcg agacatttca   7200
gttgttgggt cgaaagatca aacccaagat agtatgagtc taaagacatt gtgttggaaa   7260
cctctcttgt ctgtctctga attactgaac acaacatact agtcgtacgg ttttattttt   7320
tacttatatt gctggtaggg taaaaaaata taactcctag gaataggttg tctatatgtt   7380
tttgtcttgc ttctataatt gtaacaaaca aggaaaggga aaatactggg tgtaaaagcc   7440
attgagtcaa gttaggtcat ccctttata caaaattttt caattttttt tccaagattc     7500
ttgtacgatt aattattttt tttttgcgtc ctacagcgtg atgaaaattt ccgcctgctg    7560
caagatgagc gggaacgggc gaaatgtgca cgcgcacaac ttacgaaacg cggatgagtc   7620
actgacagcc accgcagagg ttctgactcc tactgagctc tattggaggt ggcagaaccg   7680
gtaccggagg agaccgctat aaccggtttg aatttattgt cacagtgtca catcagcggc   7740
aactcagaag tttgacagca agcaagttca tcattcgaac tagccttatt gttttagttc   7800
agtgacagcg aactgccgta ctcgatgctt tatttctcac ggtagagcgg aagaacagat   7860
aggggcagcg tgagaagagt tagaaagtaa atttttatca cgtctgaagt attcttattc   7920
ataggaaatt ttgcaaggtt ttttagctca ataacgggct aagttatata aggtgttcac   7980
gcgattttct tgttatgtat acctcttctg gcgcgcctct ttttattaac cttaattttt   8040
attttagatt cctgacttca actcaagacg cacagatatt ataacatctg cataataggc   8100
atttgcaaga attactcgtg agtaaggaaa gagtgaggaa ctatcgcata cctgcattta   8160
```

```
aagatgccga tttgggcgcg aatcctttat tttggcttca ccctcatact attatcaggg    8220
ccagaaaaag gaagtgtttc cctccttctt gaattgatgt taccctcata aagcacgtgg    8280
cctcttatcg agaaagaaat taccgtcgct cgtgatttgt ttgcaaaaag aacaaaactg    8340
aaaaaaccca gacacgctcg acttcctgtc ttcctattga ttgcagcttc caatttcgtc    8400
acacaacaag gtcctagcga cggctcacag gttttgtaac aagcaatcga aggttctgga    8460
atggcgggaa agggtttagt accacatgct atgatgccca ctgtgatctc cagagcaaag    8520
ttcgttcgat cgtactgtta ctctctctct ttcaaacaga attgtccgaa tcgtgtgaca    8580
acaacagcct gttctcacac actcttttct tctaaccaag ggggtggttt agtttagtag    8640
aacctcgtga aacttacatt tacatatata taaacttgca taaattggtc aatgcaagaa    8700
atacatattt ggtctttttct aattcgtagt ttttcaagtt cttagatgct ttctttttct    8760 ctttttttaca gatcatcaag gaagtaatta tctacttttt acaacaaata taaaacacgt    8820
acgactagta tgactcaatt cactgacatt gataagttgg ccgtctccac cataagaatt    8880
ttggctgtgg acaccgtatc caaggccaac tcaggtcacc caggtgctcc attgggtatg    8940
gcaccagctg cacacgttct atggagtcaa atgcgcatga acccaaccaa cccagactgg    9000
atcaacagag atagatttgt cttgtctaac ggtcacgcgg tcgcttttgtt gtattctatg    9060 ctacatttga ctggttacga tctgtctatt gaagacttga aacagttcag acagttgggt    9120
tccagaacac caggtcatcc tgaatttgag ttgccaggtg ttgaagttac taccggtcca    9180
ttaggtcaag gtatctccaa cgctgttggt atggccatgg ctcaagctaa cctggctgcc    9240
acttacaaca agccgggctt taccttgtct gacaactaca cctatgtttt cttgggtgac    9300
ggttgtttgc aagaaggtat ttcttcagaa gcttcctcct tggctggtca tttgaaattg    9360
ggtaacttga ttgccatcta cgatgacaac aagatcacta tcgatggtgc taccagtatc    9420
tcattcgatg aagatgttgc taagagatac gaagcctacg gttgggaagt tttgtacgta    9480
gaaaatggta acgaagatct agccggtatt gccaaggcta ttgctcaagc taagttatcc    9540
aaggacaaac caactttgat caaaatgacc acaaccattg gttacggttc cttgcatgcc    9600
ggctctcact ctgtgcacgg tgccccattg aaagcagatg atgttaaaca actaaagagc    9660
aaattcggtt tcaacccaga caagtccttt gttgttccac aagaagttta cgaccactac    9720
caaaagacaa ttttaaagcc aggtgtcgaa gccaacaaca gtggaacaa gttgttcagc    9780 gaataccaaa agaaattccc agaattaggt gctgaattgg ctagaagatt gagcggccaa    9840
ctacccgcaa attgggaatc taagttgcca acttacaccg ccaaggactc tgccgtggcc    9900
actagaaaat tatcagaaac tgttcttgag gatgtttaca atcaattgcc agagttgatt    9960
ggtggttctg ccgatttaac accttctaac ttgaccagat ggaaggaagc ccttgacttc    10020
caacctcctt cttccggttc aggtaactac tctggtagat acattaggta cggtattaga    10080
gaacacgcta tgggtgccat aatgaacggt atttcagctt tcggtgccaa ctacaaacca    10140
tacggtggta ctttcttgaa cttcgttttct tatgctgctg gtgccgttag attgtccgct    10200
ttgtctggcc acccagttat ttgggttgct acacatgact ctatcggtgt cggtgaagat    10260
ggtccaacac atcaacctat tgaaacttta gcacacttca gatccctacc aaacattcaa    10320
gtttggagac cagctgatgg taacgaagtt tctgccgcct acaagaactc tttagaatcc    10380
aagcatactc caagtatcat tgctttgtcc agacaaaact tgccacaatt ggaaggtagc    10440
tctattgaaa gcgcttctaa gggtggttac gtactacaag atgttgctaa cccagatatt    10500
attttagtgg ctactggttc cgaagtgtct ttgagtgttg aagctgctaa gactttggcc    10560
```

```
gcaaagaaca tcaaggctcg tgttgtttct ctaccagatt tcttcacttt tgacaaacaa   10620
cccctagaat acagactatc agtcttacca gacaacgttc caatcatgtc tgttgaagtt   10680
ttggctacca catgttgggg caaatacgct catcaatcct tcggtattga cagatttggt   10740
gcctccggta aggcaccaga agtcttcaag ttcttcggtt tcaccccaga aggtgttgct   10800
gaaagagctc aaaagaccat tgcattctat aagggtgaca agctaatttc tcctttgaaa   10860
aaagctttct aaattctgat cgtagatcat cagatttgat atgatattat ttgtgaaaaa   10920
atgaaataaa actttataca acttaaatac aacttttttt ataaacgatt aagcaaaaaa   10980
atagtttcaa acttttaaca atattccaaa cactcagtcc ttttccttct tatattatag   11040
gtgtacgtat tatagaaaaa tttcaatgat tactttttct ttcttttttcc ttgtaccagc   11100 acatggccga gcttgaatgt taaacccttc gagagaatca caccattcaa gtataaagcc   11160
aataaagaat ataactccta aaaggctaat tgaaaccctg tgattttttgc ccgggtttaa   11220 ggcgcgccct ttatcattat caatactgcc atttcaaaga atacgtaaat aattaatagt   11280
agtgattttc ctaactttat ttagtcaaaa aattagcctt ttaattctgc tgtaacccgt   11340
acatgcccaa aatagggggc gggttacaca gaatatataa catcgtaggt gtctgggtga   11400
acagtttatt cctggcatcc actaaatata atggagcccg ctttttaagc tggcatccag   11460 aaaaaaaag aatcccagca ccaaaatatt gttttcttca ccaaccatca gttcataggt   11520
ccattctctt agcgcaacta cagagaacag gggcacaaac aggcaaaaaa cgggcacaac   11580
ctcaatggag tgatgcaacc tgcctggagt aaatgatgac acaaggcaat tgacccacgc   11640
atgtatctat ctcatttttct tacaccttct attaccttct gctctctctg atttggaaaa   11700
agctgaaaaa aaaggttgaa accagttccc tgaaattatt cccctacttg actaataagt   11760
atataaagac ggtaggtatt gattgtaatt ctgtaaatct atttcttaaa cttcttaaat   11820
tctactttta tagttagtct ttttttttagt tttaaaacac caagaactta gtttcgaata   11880
aacacacata aacaaacacc actagcatgg ctgccggtgt cccaaaaatt gatgcgttag   11940
aatctttggg caatcctttg gaggatgcca agagagctgc agcatacaga gcagttgatg   12000
aaaatttaaa atttgatgat cacaaaatta ttggaattgg tagtggtagc acagtggttt   12060
atgttgccga aagaattgga caatatttgc atgaccctaa attttatgaa gtagcgtcta   12120
aattcatttg cattccaaca ggattccaat caagaaactt gattttggat aacaagttgc   12180
aattaggctc cattgaacag tatcctcgca ttgatatagc gtttgacggt gctgatgaag   12240
tggatgagaa tttacaatta attaaaggtg gtggtgcttg tctatttcaa gaaaaattgg   12300
ttagtactag tgctaaaacc ttcattgtcg ttgctgattc aagaaaaaag tcaccaaaac   12360
atttaggtaa gaactggagg caaggtgttc ccattgaaat tgtaccttcc tcatacgtga   12420
gggtcaagaa tgatctatta gaacaattgc atgctgaaaa agttgacatc agacaaggag   12480
gttctgctaa agcaggtcct gttgtaactg acaataataa cttcattatc gatgcggatt   12540
tcggtgaaat ttccgatcca agaaaattgc atagagaaat caaactgtta gtgggcgtgg   12600
tggaaacagg tttattcatc gacaacgctt caaaagccta cttcggtaat tctgacggta   12660
gtgttgaagt taccgaaaag tgagcggccg cgtgaattta ctttaaatct tgcattttaaa   12720 taaattttct ttttatagct ttatgactta gtttcaattt atatactatt ttaatgacat   12780
tttcgattca ttgattgaaa gctttgtgtt ttttcttgat gcgctattgc attgttcttg   12840 tcttttttcgc cacatgtaat atctgtagta gatacctgat acattgtgga tgctgagtga   12900
```

```
aattttagtt aataatggag gcgctcttaa taattttggg gatattggct ttttttttta    12960
aagtttacaa atgaattttt tccgccagga taacgattct gaagttactc ttagcgttcc    13020
tatcggtaca gccatcaaat catgcctata aatcatgcct atatttgcgt gcagtcagta    13080
tcatctacat gaaaaaaact cccgcaattt cttatagaat acgttgaaaa ttaaatgtac    13140
gcgccaagat aagataacat atatctagat gcagtaatat acacagattc ccgcggacgt    13200
gggaaggaaa aaattagata acaaaatctg agtgatatgg aaattccgct gtatagctca    13260
tatctttccc tccaccgcgg tggtcgactt tcacatacgt tgcatacgtc gatatagata    13320
ataatgataa tgacagcagg attatcgtaa tacgtaatag ctgaaaatct caaaaatgtg    13380
tgggtcatta cgtaaataat gataggaatg ggattcttct atttttcctt tttccattct    13440
agcagccgtc gggaaaacgt ggcatcctct ctttcgggct caattggagt cacgctgccg    13500
tgagcatcct ctcttttccat atctaacaac tgagcacgta accaatggaa aagcatgagc    13560
ttagcgttgc tccaaaaaag tattggatgg ttaataccat ttgtctgttc tcttctgact    13620
ttgactcctc aaaaaaaaaa atctacaatc aacagatcgc ttcaattacg ccctcacaaa    13680
aacttttttc cttcttcttc gcccacgtta aattttatcc ctcatgttgt ctaacggatt    13740
tctgcacttg atttattata aaagacaaa gacataaac ttctctatca atttcagtta    13800
ttgttcttcc ttgcgttatt cttctgttct tcttttcctt ttgtcatata taaccataac    13860
caagtaatac atattcaaac ttaagactcg agatggtcaa accaattata gctcccagta    13920
tccttgcttc tgacttcgcc aacttgggtt gcgaatgtca taaggtcatc aacgccggcg    13980
cagattggtt acatatcgat gtcatggacg gccattttgt tccaaacatt actctgggcc    14040
aaccaattgt tacctcccta cgtcgttctg tgccacgccc tggcgatgct agcaacacag    14100
aaaagaagcc cactgcgttc ttcgattgtc acatgatggt tgaaaatcct gaaaaatggg    14160
tcgacgattt tgctaaatgt ggtgctgacc aatttacgtt ccactacgag gccacacaag    14220 acccctttgca tttagttaag ttgattaagt ctaagggcat caaagctgca tgcgccatca    14280
aacctggtac ttctgttgac gtttatttg aactagctcc tcatttggat atggctcttg    14340
ttatgactgt ggaacctggg tttggaggcc aaaaattcat ggaagacatg atgccaaaag    14400
tggaaacttt gagagccaag ttcccccatt tgaatatcca agtcgatggt ggtttgggca    14460
aggagaccat cccgaaagcc gccaaagccg gtgccaacgt tattgtcgct ggtaccagtg    14520
ttttcactgc agctgacccg cacgatgtta tctccttcat gaaagaagaa gtctcgaagg    14580
aattgcgttc tagagatttg ctagattaga cgtctgttta aagattacgg atatttaact    14640
tacttagaat aatgccattt ttttgagtta taataatcct acgttagtgt gagcgggatt    14700
taaactgtga ggaccttaat acattcagac acttctgcgg tatcacccta cttattccct    14760
tcgagattat atctaggaac ccatcaggtt ggtggaagat tacccgttct aagacttttc    14820
agcttcctct attgatgtta cacctggaca cccctttctc ggcatccagt ttttaatctt    14880
cagtggcatg tgagattctc cgaaattaat taaagcaatc acacaattct ctcggatacc    14940
acctcggttg aaactgacag gtggtttgtt acgcatgcta atgcaaagga gcctatatac    15000
ctttggctcg gctgctgtaa cagggaatat aaagggcagc ataatttagg agtttagtga    15060
acttgcaaca tttactattt tccttcttta cgtaaatatt tttcttttta attctaaatc    15120 aatcttttc aatttttgt ttgtattctt ttcttgctta aatctataac tacaaaaaac    15180
acatacataa actaaaacgt acgactagta tgtctgaacc agctcaaaag aaacaaaagg    15240
ttgctaacaa ctctctagaa caattgaaag cctccggcac tgtcgttgtt gccgacactg    15300
```

```
gtgatttcgg ctctattgcc aagtttcaac ctcaagactc cacaactaac ccatcattga    15360
tcttggctgc tgccaagcaa ccaacttacg ccaagttgat cgatgttgcc gtggaatacg    15420
gtaagaagca tggtaagacc accgaagaac aagtcgaaaa tgctgtggac agattgttag    15480
tcgaattcgg taaggagatc ttaaagattg ttccaggcag agtctccacc gaagttgatg    15540
ctagattgtc ttttgacact caagctacca ttgaaaaggc tagacatatc attaaattgt    15600
ttgaacaaga aggtgtctcc aaggaaagag tccttattaa aattgcttcc acttgggaag    15660
gtattcaagc tgccaaagaa ttggaagaaa aggacggtat ccactgtaat tgactctat    15720 tattctcctt cgttcaagca gttgcctgtg ccgaggccca agttactttg atttccccat    15780
ttgttggtag aattctagac tggtacaaat ccagcactgg taaagattac aagggtgaag    15840
ccgacccagg tgttatttcc gtcaagaaaa tctacaacta ctacaagaag tacgttacaa    15900
agactattgt tatgggtgct tctttcagaa gcactgacga atcaaaaac ttggctggtg     15960 ttgactatct aacaatttct ccagctttat tggacaagtt gatgaacagt actgaacctt    16020
tcccaagagt tttggaccct gtctccgcta agaaggaagc cggcgacaag atttcttaca    16080
tcagcgacga atctaaattc agattcgact tgaatgaaga cgctatggcc actgaaaaat    16140
tgtccgaagg tatcagaaaa ttctctgccg atattgttac tctattcgac ttgattgaaa    16200
agaaagttac cgcttaagga agtatctcgg aaatattaat ttaggccatg tccttatgca    16260
cgtttctttt gatacttacg ggtacatgta cacaagtata tctatatata taaattaatg    16320
aaaatcccct atttatatat atgacttaa cgagacagaa cagtttttta ttttttatcc     16380
tatttgatga atgatacagt ttcg                                          16404

<210> SEQ ID NO 19
<211> LENGTH: 95
<212> TYPE: DNA
<213> ORGANISM: Artificial sequence
<220> FEATURE:
<223> OTHER INFORMATION: URA3 deletion scar

<400> SEQUENCE: 19
gcattgcgga ttacgtattc taatgttcag ataacttcgt atagcataca ttatacgaag    60
ttatccagtg atgatacaac gagttagcca aggtg                              95

<210> SEQ ID NO 20
<211> LENGTH: 100
<212> TYPE: DNA
<213> ORGANISM: Saccharomyces cerevisiae

<400> SEQUENCE: 20
gtccataaag cttttcaatt catctttttt ttttttgttc ttttttttga ttccggtttc    60
tttgaaattt ttttgattcg gtaatctccg agcagaagga                         100

<210> SEQ ID NO 21
<211> LENGTH: 100
<212> TYPE: DNA
<213> ORGANISM: Saccharomyces cerevisiae

<400> SEQUENCE: 21
aaaactgtat tataagtaaa tgcatgtata ctaaactcac aaattagagc ttcaatttaa    60
ttatatcagt tattacccgg gaatctcggt cgtaatgatt                         100

<210> SEQ ID NO 22
```

```
<211> LENGTH: 100
<212> TYPE: DNA
<213> ORGANISM: Saccharomyces cerevisiae

<400> SEQUENCE: 22
attggcatta tcacataatg aattatacat tatataaagt aatgtgatttt cttcgaagaa    60 tatactaaaa aatgagcagg caagataaac gaaggcaaag                          100

<210> SEQ ID NO 23
<211> LENGTH: 100
<212> TYPE: DNA
<213> ORGANISM: Saccharomyces cerevisiae

<400> SEQUENCE: 23
tagtgacacc gattatttaa agctgcagca tacgatatat atacatgtgt atatatgtat    60
acctatgaat gtcagtaagt atgtatacga acagtatgat                          100

<210> SEQ ID NO 24
<211> LENGTH: 6728
<212> TYPE: DNA
<213> ORGANISM: Artificial sequence
<220> FEATURE:
<223> OTHER INFORMATION: constructed vector

<400> SEQUENCE: 24
acatatttga atgtatttag aaaaataaac aaataggggt tccgcgcaca tttccccgaa    60
aagtgccacc tgggtccttt tcatcacgtg ctataaaaat aattataatt taaattttttt  120 aatataaata tataaattaa aaatagaaag taaaaaaaga aattaaagaa aaaatagttt   180
ttgttttccg aagatgtaaa agactctagg gggatcgcca acaaatacta cctttatct   240 tgctcttcct gctctcaggt attaatgccg aattgtttca tcttgtctgt gtagaagacc  300
acacacgaaa atcctgtgat tttacatttt acttatcgtt aatcgaatgt atatctattt  360
aatctgcttt tcttgtctaa taaatatata tgtaaagtac gctttttgtt gaaatttttt  420
aaacctttgt ttatttttttt ttcttcattc cgtaactctt ctaccttctt tatttacttt  480
ctaaaatcca aatacaaaac ataaaaataa ataaacacag agtaaattcc caaattattc  540
catcattaaa agatacgagg cgcgtgtaag ttacaggcaa gcgatccgtc ctaagaaacc  600
attattatca tgacattaac ctataaaaat aggcgtatca cgaggccctt tcgtctcgcg  660
cgtttcggtg atgacggtga aaacctctga cacatgcagc tcccggagac ggtcacagct  720
tgtctgtaag cggatgccgg gagcagacaa gcccgtcagg gcgcgtcagc gcgtgttggc  780
gggtgtcggg gctggcttaa ctatgcggca tcagagcaga ttgtactgag agtgcaccat  840
aaattcccgt tttaagagct tggtgagcgc taggagtcac tgccaggtat cgtttgaaca  900
cggcattagt cagggaagtc ataacacagt cctttcccgc aattttctttt tctattact   960 cttggcctcc tctagtacac tctatatttt tttatgcctc ggtaatgatt tcatttttt  1020 tttttcccct agcggatgac tctttttttt tcttagcgat tggcattatc acataatgaa 1080
ttatacatta tataaagtaa tgtgatttct tcgaagaata tactaaaaaa tgagcaggca 1140
agataaacga aggcaaagat gacagagcag aaagccctag taaagcgtat tacaaatgaa 1200
accaagattc agattgcgat ctcttttaaag ggtggtcccc tagcgataga gcactcgatc 1260
ttcccagaaa aagaggcaga agcagtagca gaacaggcca cacaatcgca agtgattaac 1320
gtccacacag gtatagggtt tctggaccat atgatacatg ctctggccaa gcattccggc 1380
tggtcgctaa tcgttgagtg cattggtgac ttacacatag acgaccatca caccactgaa 1440
```

```
gactgcggga ttgctctcgg tcaagctttt aaagaggccc tactggcgcg tggagtaaaa      1500
aggtttggat caggatttgc gcctttggat gaggcacttt ccagagcggt ggtagatctt      1560
tcgaacaggc cgtacgcagt tgtcgaactt ggtttgcaaa gggagaaagt aggagatctc      1620
tcttgcgaga tgatcccgca ttttcttgaa agctttgcag aggctagcag aattaccctc      1680
cacgttgatt gtctgcgagg caagaatgat catcaccgta gtgagagtgc gttcaaggct      1740
cttgcggttg ccataagaga agccacctcg cccaatggta ccaacgatgt tccctccacc      1800
aaaggtgttc ttatgtagtg acaccgatta tttaaagctg cagcatacga tatatataca      1860
tgtgtatata tgtataccta tgaatgtcag taagtatgta tacgaacagt atgatactga      1920
agatgacaag gtaatgcatc attctatacg tgtcattctg aacgaggcgc gctttccttt      1980 tttcttttg cttttctt tttttctct tgaactcgac ggatctatgc ggtgtgaaat      2040
accgcacaga tgcgtaagga gaaataccg catcaggaaa ttgtaaacgt taatatttg      2100 ttaaaattcg cgttaaattt tgttaaatc agctcatttt ttaaccaata ggccgaaatc      2160
ggcaaaatcc cttataaatc aaaagaatag accgagatag ggttgagtgt tgttccagtt      2220
tggaacaaga gtccactatt aaagaacgtg gactccaacg tcaaagggcg aaaaaccgtc      2280
tatcagggcg atggcccact acgtgaacca tcaccctaat caagttttt ggggtcgagg      2340 tgccgtaaag cactaaatcg gaaccctaaa gggagccccc gatttagagc ttgacgggga      2400
aagccggcga acgtggcgag aaaggaaggg aagaagcga aaggagcggg cgctagggcg      2460
ctggcaagtg tagcggtcac gctgcgcgta accaccacac ccgccgcgct taatgcgccg      2520
ctacagggcg cgtcgcgcca ttcgccattc aggctgcgca actgttggga agggcgatcg      2580
gtgcgggcct cttcgctatt acgccagctg gcgaaagggg gatgtgctgc aaggcgatta      2640
agttgggtaa cgccagggtt tcccagtca cgacgttgta aaacgacggc cagtgagcgc      2700
gcgtaatacg actcactata gggcgaattg ggtaccgggc ccccctcga ggtcgacggt      2760 atcgataagc ttgattagaa gccgccgagc gggcgacagc cctccgacgg aagactctcc      2820
tccgtgcgtc ctcgtcttca ccggtcgcgt tcctgaaacg cagatgtgcc tcgcgccgca      2880
ctgctccgaa caataaagat tctacaatac tagctttat ggttatgaag aggaaaaatt      2940
ggcagtaacc tggccccaca aaccttcaaa ttaacgaatc aaattaacaa ccataggatg      3000
ataatgcgat tagttttta gccttatttc tggggtaatt aatcagcgaa gcgatgattt      3060
ttgatctatt aacagatata taaatggaaa agctgcataa ccactttaac taatactttc      3120
aacattttca gtttgtatta cttcttattc aaatgtcata aaagtatcaa caaaaattg      3180 ttaatatacc tctatacttt aacgtcaagg agaaaatgt ccaatttact gcccgtacac      3240
caaaatttgc ctgcattacc ggtcgatgca acgagtgatg aggttcgcaa gaacctgatg      3300
gacatgttca gggatcgcca ggcgttttct gagcatacct ggaaaatgct tctgtccgtt      3360
tgccggtcgt gggcggcatg gtgcaagttg aataaccgga aatggtttcc cgcagaacct      3420
gaagatgttc gcgattatct tctatatctt caggcgcgcg gtctggcagt aaaaactatc      3480
cagcaacatt tgggccagct aaacatgctt catcgtcggt ccgggctgcc acgaccaagt      3540
gacagcaatg ctgtttcact ggttatgcgg cggatccgaa agaaaacgt tgatgccggt      3600 gaacgtgcaa acaggctct agcgttcgaa cgcactgatt tcgaccaggt tcgttcactc      3660
atggaaaata gcgatcgctg ccaggatata cgtaatctgg catttctggg gattgcttat      3720
aacaccctgt tacgtatagc cgaaattgcc aggatcaggg ttaaagatat ctcacgtact      3780
```

```
gacggtggga gaatgttaat ccatattggc agaacgaaaa cgctggttag caccgcaggt   3840
gtagagaagg cacttagcct gggggtaact aaactggtcg agcgatggat ttccgtctct   3900
ggtgtagctg atgatccgaa taactacctg ttttgccggg tcagaaaaaa tggtgttgcc   3960
gcgccatctg ccaccagcca gctatcaact cgcgccctgg aagggatttt tgaagcaact   4020
catcgattga tttacggcgc taaggatgac tctggtcaga gatacctggc ctggtctgga   4080
cacagtgccc gtgtcggagc cgcgcgagat atggcccgcg ctggagtttc aataccggag   4140
atcatgcaag ctggtggctg gaccaatgta atattgtca tgaactatat ccgtaacctg   4200
gatagtgaaa caggggcaat ggtgcgcctg ctggaagatg gcgattagga gtaagcgaat   4260
ttcttatgat ttatgatttt tattattaaa taagttataa aaaaaataag tgtatacaaa   4320
ttttaaagtg actcttaggt tttaaaacga aaattcttat tcttgagtaa ctctttcctg   4380
taggtcaggt tgctttctca ggtatagcat gaggtcgctc ttattgacca cacctctacc   4440
ggcatgccga gcaaatgcct gcaaatcgct ccccatttca cccaattgta gatatgctaa   4500
ctccagcaat gagttgatga atctcggtgt gtattttatg tcctcagagg acaacacctg   4560
tggtgttcta gagcggccgc caccgcggtg gagctccagc ttttgttccc tttagtgagg   4620
gttaattgcg cgcttggcgt aatcatggtc atagctgttt cctgtgtgaa attgttatcc   4680
gctcacaatt ccacacaaca taggagccgg aagcataaag tgtaaagcct ggggtgccta   4740
atgagtgagg taactcacat taattgcgtt gcgctcactg cccgctttcc agtcgggaaa   4800
cctgtcgtgc cagctgcatt aatgaatcgg ccaacgcgcg gggagaggcg gtttgcgtat   4860
tgggcgctct tccgcttcct cgctcactga ctcgctgcgc tcggtcgttc ggctgcggcg   4920
agcggtatca gctcactcaa aggcggtaat acggttatcc acagaatcag gggataacgc   4980
aggaaagaac atgtgagcaa aaggccagca aaaggccagg aaccgtaaaa aggccgcgtt   5040
gctggcgttt ttccataggc tccgcccccc tgacgagcat cacaaaaatc gacgctcaag   5100
tcagaggtgg cgaaacccga caggactata aagataccag gcgtttcccc ctggaagctc   5160
cctcgtgcgc tctcctgttc cgaccctgcc gcttaccgga tacctgtccg cctttctccc   5220
ttcgggaagc gtggcgcttt ctcatagctc acgctgtagg tatctcagtt cggtgtaggt   5280
cgttcgctcc aagctgggct gtgtgcacga accccccgtt cagcccgacc gctgcgcctt   5340
atccggtaac tatcgtcttg agtccaaccc ggtaagacac gacttatcgc cactggcagc   5400
agccactggt aacaggatta gcagagcgag gtatgtaggc ggtgctacag agttcttgaa   5460
gtggtggcct aactacggct acactagaag gacagtattt ggtatctgcg ctctgctgaa   5520
gccagttacc ttcggaaaaa gagttggtag ctcttgatcc ggcaaacaaa ccaccgctgg   5580
tagcggtggt ttttttgttt gcaagcagca gattacgcgc agaaaaaaag gatctcaaga   5640
agatcctttg atcttttcta cggggtctga cgctcagtgg aacgaaaact cacgttaagg   5700
gattttggtc atgagattat caaaaaggat cttcacctag atccttttaa attaaaaatg   5760
aagttttaaa tcaatctaaa gtatatatga gtaaacttgg tctgacagtt accaatgctt   5820
aatcagtgag gcacctatct cagcgatctg tctatttcgt tcatccatag ttgcctgact   5880
ccccgtcgtg tagataacta cgatacggga gggcttacca tctggcccca gtgctgcaat   5940
gataccgcga cccacgctca ccggctcca agatttatca gcaataaacc agccagccgg   6000
aagggccgag cgcagaagtg gtcctgcaac tttatccgcc tccatccagt ctattaattg   6060
ttgccgggaa gctagagtaa gtagttcgcc agttaatagt ttgcgcaacg ttgttgccat   6120
tgctacaggc atcgtggtgt cacgctcgtc gtttggtatg gcttcattca gctccggttc   6180
```

```
ccaacgatca aggcgagtta catgatcccc catgttgtgc aaaaaagcgg ttagctcctt    6240
cggtcctccg atcgttgtca gaagtaagtt ggccgcagtg ttatcactca tggttatggc    6300
agcactgcat aattctctta ctgtcatgcc atccgtaaga tgcttttctg tgactggtga    6360
gtactcaacc aagtcattct gagaatagtg tatgcggcga ccgagttgct cttgcccggc    6420
gtcaatacgg gataataccg cgccacatag cagaacttta aaagtgctca tcattggaaa    6480
acgttcttcg gggcgaaaac tctcaaggat cttaccgctg ttgagatcca gttcgatgta    6540
acccactcgt gcacccaact gatcttcagc atcttttact ttcaccagcg tttctgggtg    6600
agcaaaaaca ggaaggcaaa atgccgcaaa aaagggaata agggcgacac ggaaatgttg    6660
aatactcata ctcttccttt ttcaatatta ttgaagcatt tatcagggtt attgtctcat    6720
gagcggat                                                              6728
```